United States Patent
Kopelman et al.

(10) Patent No.: US 9,816,993 B2
(45) Date of Patent: Nov. 14, 2017

(54) MAGNETICALLY INDUCED MICROSPINNING FOR SUPER-DETECTION AND SUPER-CHARACTERIZATION OF BIOMARKERS AND LIVE CELLS

(75) Inventors: Raoul Kopelman, Ann Arbor, MI (US); Remy Elbez, Ann Arbor, MI (US); Ariel Hecht, Ann Arbor, MI (US); Brandon H. McNaughton, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 10 days.

(21) Appl. No.: 14/111,142

(22) PCT Filed: Apr. 11, 2012

(86) PCT No.: PCT/US2012/033152
§ 371 (c)(1),
(2), (4) Date: Jan. 24, 2014

(87) PCT Pub. No.: WO2012/142179
PCT Pub. Date: Oct. 18, 2012

(65) Prior Publication Data
US 2014/0248632 A1  Sep. 4, 2014

Related U.S. Application Data

(60) Provisional application No. 61/474,116, filed on Apr. 11, 2011, provisional application No. 61/474,113, filed on Apr. 11, 2011.

(51) Int. Cl.
*G01N 33/574* (2006.01)
*G01N 27/84* (2006.01)
(Continued)

(52) U.S. Cl.
CPC .......... *G01N 33/574* (2013.01); *G01N 27/84* (2013.01); *G01N 33/54333* (2013.01); *G01N 33/587* (2013.01)

(58) Field of Classification Search
CPC .......... G01N 33/574; G01N 33/54333; G01N 27/84; G01N 33/587; G01N 2021/825
See application file for complete search history.

(56) References Cited

U.S. PATENT DOCUMENTS 3,676,679 A   7/1972  Waters
4,778,758 A   10/1988 Ericsson et al.
(Continued)

FOREIGN PATENT DOCUMENTS

WO   WO-00/67037 A2   11/2000
WO   WO-01/14591 A1   3/2001
(Continued)

OTHER PUBLICATIONS

Agayan et al., Optical Manipulation of Metal-Silica Hybrid Nanoparticles, Proceedings of SPIE, 5514:502-513 (2004).
(Continued)

*Primary Examiner* — Gail R Gabel
(74) *Attorney, Agent, or Firm* — Marshall, Gerstein & Borun LLP

(57) ABSTRACT

Identification, quantification and characterization of biological micro- and nano-systems is enabled by magnetically spinning these natural, non-magnetic systems with the aid of induced magnetization. Biofriendly magnetic micro- and nano-labels enable magnetorotation in extremely weak electromagnetic fields. The spinning of these micromotors can be observed by a simple, CD-like, optical tracking system. The spinning frequency response enables real-time monitoring of single (cancer) cell morphology, with sub-microscopic resolution, yielding previously undeterminable infor-
(Continued)

mation. Likewise, it enables super-low detection limits for any (cancer) biomarker.

25 Claims, 21 Drawing Sheets

(51) Int. Cl.
  *G01N 33/58* (2006.01)
  *G01N 33/543* (2006.01)

(56) References Cited

U.S. PATENT DOCUMENTS

| | | | |
|---|---|---|---|
| 5,171,534 A | 12/1992 | Smith et al. | |
| 5,232,839 A | 8/1993 | Eden et al. | |
| 5,252,493 A | 10/1993 | Fujiwara et al. | |
| 5,293,210 A | 3/1994 | Berndt | |
| 5,336,600 A | 8/1994 | Monget | |
| 5,374,527 A | 12/1994 | Grossman | |
| 5,434,056 A | 7/1995 | Monget et al. | |
| 5,516,670 A | 5/1996 | Kuehnle et al. | |
| 5,534,527 A | 7/1996 | Black et al. | |
| 5,593,854 A | 1/1997 | Berndt | |
| 5,716,798 A | 2/1998 | Monthony et al. | |
| 5,770,388 A | 6/1998 | Vorpahl | |
| 5,770,440 A | 6/1998 | Berndt | |
| 5,814,474 A | 9/1998 | Berndt | |
| 5,888,760 A | 3/1999 | Godsey et al. | |
| 5,910,300 A | 6/1999 | Tournier et al. | |
| 5,998,224 A | 12/1999 | Rohr et al. | |
| 5,998,517 A | 12/1999 | Gentle, Jr. et al. | |
| 6,002,817 A | 12/1999 | Kopelman et al. | |
| 6,027,946 A | 2/2000 | Weitschies et al. | |
| 6,096,272 A | 8/2000 | Clark et al. | |
| 6,107,102 A | 8/2000 | Ferrari | |
| 6,143,558 A | 11/2000 | Kopelman et al. | |
| 6,159,686 A | 12/2000 | Kardos et al. | |
| 6,275,031 B1 | 8/2001 | Simmonds | |
| 6,372,485 B1 | 4/2002 | Clark et al. | |
| 6,395,506 B1 | 5/2002 | Pitner et al. | |
| 6,437,563 B1 | 8/2002 | Simmonds et al. | |
| 6,518,747 B2 | 2/2003 | Sager et al. | |
| 6,586,259 B1 | 7/2003 | Mahan et al. | |
| 6,596,532 B1 | 7/2003 | Hyman et al. | |
| 6,597,176 B2 | 7/2003 | Simmonds et al. | |
| 6,632,655 B1 | 10/2003 | Mehta et al. | |
| 6,660,381 B2 | 12/2003 | Halas et al. | |
| 6,777,226 B2 | 8/2004 | Jeffrey et al. | |
| 6,780,581 B2 | 8/2004 | Vesey et al. | |
| 6,825,655 B2 | 11/2004 | Minchole et al. | |
| 6,900,030 B2 | 5/2005 | Pitner et al. | |
| 6,927,570 B2 | 8/2005 | Simmonds et al. | |
| 7,115,384 B2 | 10/2006 | Clark et al. | |
| 7,183,073 B2 | 2/2007 | Hyman et al. | |
| 7,323,139 B2 | 1/2008 | LaBorde et al. | |
| 7,341,841 B2 | 3/2008 | Metzger et al. | |
| 7,547,554 B2 | 6/2009 | Odefey | |
| 7,564,245 B2 | 7/2009 | Lee | |
| 7,575,934 B2 | 8/2009 | Atwood | |
| 7,691,600 B2 | 4/2010 | Mercader Badia et al. | |
| 8,846,331 B2 * | 9/2014 | McNaughton et al. | 435/29 |
| 2002/0150914 A1 | 10/2002 | Andersen et al. | |
| 2003/0012693 A1 | 1/2003 | Otillar et al. | |
| 2003/0076087 A1 | 4/2003 | Minchole et al. | |
| 2003/0124516 A1 | 7/2003 | Chung et al. | |
| 2003/0169032 A1 | 9/2003 | Minchole et al. | |
| 2004/0033627 A1 | 2/2004 | Aytur et al. | |
| 2004/0058458 A1 | 3/2004 | Anker et al. | |
| 2005/0048672 A1 | 3/2005 | Luxton et al. | |
| 2006/0008924 A1 | 1/2006 | Anker et al. | |
| 2006/0057578 A1 | 3/2006 | Willner et al. | |
| 2006/0160171 A1 | 7/2006 | Bachur et al. | |
| 2006/0210987 A1 | 9/2006 | Gleich | |
| 2007/0020720 A1 | 1/2007 | Colin et al. | |
| 2007/0037225 A1 | 2/2007 | Metzger et al. | |
| 2007/0205767 A1 | 9/2007 | Xu et al. | |
| 2008/0038769 A1 | 2/2008 | Bernardi et al. | |
| 2008/0220411 A1 * | 9/2008 | McNaughton et al. | 435/5 |
| 2009/0085557 A1 | 4/2009 | Krozer et al. | |
| 2009/0136953 A1 | 5/2009 | Gold et al. | |
| 2009/0269854 A1 | 10/2009 | Kageyama | |
| 2010/0033158 A1 | 2/2010 | Dittmer et al. | |
| 2010/0068755 A1 | 3/2010 | Walsh et al. | |
| 2010/0072994 A1 | 3/2010 | Lee et al. | |
| 2010/0129857 A1 | 5/2010 | Walsh et al. | |
| 2012/0164680 A1 | 6/2012 | McNaughton et al. | |
| 2013/0337455 A1 | 12/2013 | McNaughton et al. | |

FOREIGN PATENT DOCUMENTS

| | | |
|---|---|---|
| WO | WO-03/19188 A1 | 3/2003 |
| WO | WO-2006/104700 A1 | 10/2006 |
| WO | WO-2007/120095 A1 | 10/2007 |
| WO | WO-2008/075285 A1 | 6/2008 |
| WO | WO-2009/037636 A1 | 3/2009 |
| WO | WO-2010/026551 A1 | 3/2010 |
| WO | WO-2010/041178 A1 | 4/2010 |
| WO | WO-2010/048511 A1 | 4/2010 |
| WO | WO-2011/021142 A1 | 2/2011 |
| WO | WO-2012/027747 A2 | 3/2012 |

OTHER PUBLICATIONS

Anker et al., Magnetically Modulated Optical Nanoprobes, Appl. Phys. Letts., 82:1102-1104 (2003).

Astalan et al., Biomolecular Reactions Studied Using Changes in Brownian Rotation Dynamics of Magnetic Particles, Biosensors and Bioelectronics, 19:945-951 (2004).

Bao et al., Cell and Molecular Mechanics of Biological Materials, Nat. Mat., 2:715-725 (2003).

Behrend et al., Brownian Modulated Optical Nanoprobes, Appl. Phys. Letts., 84:154-156 (2004).

Behrend et al., Microheology with Modulated Optical Nanoprobes (MOONs), J. Magnetism and Magnetic Mats., 293:663-670 (2005).

Bhiladvala et al., Effect of Fluids on the Q Factor and Resonance Frequency of Oscillating Micrometer and Nanometer Scale Beams, Phys. Rev. E, 69:36307-1-36307-5 (2004).

Biswal et al., Micromixing with linked chains of paramagnetic particles, Anal. Chem., 76:6448- 55 (2004).

Bornhop et al., Advance in contrast agents, reporters, and detection, J. Biomed. Optics, 6(2):106-115 (2001).

Boucher et al., Bad bugs, no drugs: no Eskape! An update from the Infectious Diseases Society of America, Clin. Infect. Dis., 48(1):1-12 (2009).

Boucher et al., Epidemiology of methicillin-resistant Staphylococcus aureus, Clin. Infect. Dis., 46 Suppl 5:S344-9 (2008).

Cebers, Dynamics of an Active Magentic Particle in a Rotating Magentic Field, Phys. Rev. E., 73:021505-1-021505-5 (2006).

Chu et al., *Staphylococcus aureus* bacteremia in patients with prosthetic devices: costs and outcomes, Am. J. Med., 118(12):1416 (2005).

Connolly et al., Experimental Evaluation of the Magnetic Properties of Commerically Available Magnetic Microspheres, Bio-Medical Materials and Engineering, 15:421-31 (2005).

Crick, The Physical Properties of Cytoplasm. A Study by Means of the Magnetic Particle Method. Part II. Theoretical Treatment, Strangeways Research Laboratory, Cambridge, 50532 (1950).

Crick, et al., The Physical Properties of Cytoplasm a Study by Means of the Magnetic Particle Method—Part I Experimental, Strangeways Research Laboratory, 37-80 (1949).

Deresinski, Counterpoint: Vancomycin and *Staphylococcus aureus*—an antibiotic enters obsolescence, Clin. Infest. Dis., 44(12):1543-8 (2007).

Ekinci et al., Nanoelectromechanical Systems, Review of Scientific Instruments, 76:061101-1-061101-12 (2005).

Elbez et al., Nanoparticle induced cell magneto-rotation: monitoring morphology, stress and drug sensitivity of a suspended single cancer cell, PLOS One, 6(12):e28475 (2011).

(56) References Cited

OTHER PUBLICATIONS

Elfwing et al., Observing Growth and Division of Large Numbers of Individual Bacteria by Image Analysis, Applied and Environmental Microbiology, 70(2):675-78 (2004).
Fennimore et al., Rotational Actuators based on Carbon Nanotubes, Nature, 424:408-10 (2003).
Fratamico et al., Detection of *Escherichia coli* 0157:H7 using a surface plasmon resonance biosensor, Biotechnology Techniques, 12(7):571-6 (1998).
Fujinami et al., Sensitive detection of bacteria and spores using a portable bioluminescence ATP measurement assay system distinguishing from white powder materials, J. Health Sci., 50:126-32 (2004).
Gfeller et al., Micromechanical oscillators as rapid biosensor for the detection of active growth of *Escherichia coli*, Biosens. Biolectron., 21(3):528-33 (2005).
Gitterman et al., Order and Choas: Are They Contradictory or Complementary? Eur. J. Phys., 23:119-122 (2002).
Godin et al., Using buoyant mass to measure the growth of single cells, Nat. Methods, 7(5):387-90 (2010).
Gu et al., Using Biofunicational Magnetic Nanoparticles to Capture Gram-Negative Bacteria at an Ultra-Low Concentration, Chemical Communications, 15:1966-1967 (2003).
Hafeli et al., Characterization of Magnetic Particles and Microspheres and Their Magnetophoretic Mobility Using a Digital Microscopy Method, European Cells and Materials, 3:24-27 (2002).
Haukanes et al., Application of Magnetic Beads in Bioassays, Bio-Technology, 11:60-63 (1993).
Horvath et al., Magnetic Dimer Motion Effects in a Rotating Magnetic Field (a Qualitative Model of Magnetoviscosity and Permittivity in Magnetorheological Suspensions), Czech J. Phys., 43:671-81 (1993).
Hulteen et al., Nanosphere Lithography: A Materials General Fabrication Process for Periodic Particle Array Surfaces, J. Vac. Sci. Technol. A., 13:1553-8 (1995).
Ilic et al., Single Cell Detection with Micromechanical Oscillators, J. Vacuum Sci. & Tech. B: Microelectronics and Nanometer Structures, 19:2825-8 (2001).
Ilic et al., Virus Detection Using Nanoelectromechanical Devices, Appl. Phys. Lett., 85:2604-6 (2004).
Ilic et al., Mechanical resonant immunospecific biological detector, Appl. Phys. Lett., 77:450-2 (2000).
International Preliminary Examination Report from PCT/US2012/033152 dated Oct. 24, 2013.
International Search Report and Written Opinion, International application No. PCT/US12/33152, date Nov. 20, 2012.
Ishiyama et al., Swimming of Magnetic Micro-Machines under a Very Wide-Range of Reynolds No. Conditions, IEEE Trans. Magn., 37(4):2868-2870 (2001).
Jain, Understanding barriers to drug delivery: high resolution in vivo imaging is key, Clin. Cancer Res., 5(7):1605-606 (1999).
Janssen et al., Controlled torque on superparamagnetic beads for functional biosensors, Biosens. Bioelectron., 24(7):1937-41 (2009).
Jiang et al., A lost-wax approach to monodisperse colloids and their crystals, Science, 291 :453-457 (2001).
Kashevsky, Nonlinear Flow-Particle Interaction in Suspensions of Fine Quasi-Rigid Ferroparticles: a Giant Magnetic Effect of Fluid Rotation, J. Phys. D: Appl. Phys., 34:518-524 (2001).
Kinnunen et al., Monitoring the growth and drug susceptibility of individual bacteria using asynchronous magnetic bea rotation sensors, Biosensors and Bioelectronics, 26(5):2751-5 (2010).
Klevens et al., Changes in the epidemiology of methicillin-resistant *Staphylococcus aureus* in intensive care units in US hospitals, 1992-2003, Clin. Infest. Dis., 42(3):389-91 (2006).
Kneipp et al., Surface-Enhanced Raman Spectroscopy in Single Living Cells Using Gold Nanoparticles , Applied Spectroscopy, 56(2):150-154 (2002).
Korneva et al., Carbon Nanotubes Loaded with Magnetic Particles, Nano Lett., 5:879-884 (2005).
Koskinen et al., Development of a rapid assay methodology for antimicrobial susceptibility testing of *Staphylococcus aureus*, Diagn. Microbiol. Infect. Dis., 62(3):306-16 (2008).
Kumar et al., Duration of hypotension before initiation of effective antimicrobial therapy is the critical determinant of survival in human septic shock, Crit. Care Med., 34(6):1589-96 (2006).
Kurlyandskaya et al., Magnetic Dynabeads Detection by Sensitive Element Based on Giant Magnetoimpedance, Biosensors and Bioelectronics, 20:1611-1616 (2005).
Lapointe et al., Statis and Dynamic Properties of Magnetic Nanowires in Nematic Fluids, J. Appl. Phys., 97:10 (2005).
Lu et al., Nanophotonic Crescent Moon Structures with Sharp Edge for Ultrasensitive Biomolecular Detection by Local Electromagnetic Field Enhancement Effect, Nano Lett., 5:119-124 (2005).
MacDougall et al., Antimicrobial stewardship programs in health care systems, Clin. Microbiol. Rev., 18(4):638-56 (2005).
Mayer et al., Measurement of the Fluorescence Lifetime in Scattering Media by Frequency-Domain Photon Migration , Applied Optics, 38:4930-4938 (1999).
McNaughton et al. Sudden Breakdown in Linear Response of a Rotationally Driven Magnetic Microparticle and Application to Physical and Chemical Microsensing (J. Phys. Chem. B, 110 (38), pp. 18958-18964 (2006).
McNaughton et al., Fabrication of Uniform Half-Shell Magnetic Nanoparticles and Microspheres with Applications as Magnetically Modulated Optical Nanoprobes, arXiv:cond-mat/0506418v1, pp. 1-6 (2005).
McNaughton et al., Physiochemical Microparticle Sensors Based on Nonlinear Magnetic Oscillations, Sensors and Actuators B., 121 :330-340 (2007).
McNaughton et al., Compact sensor for measuring nonlinear rotational dynamics of driven magnetic microspheres with biomedical applications, JMMM, 321:1648-52 (2009).
McNaughton et al., Single bacterial cell detection with nonlinear rotation rate shifts of driven magnetic microspheres, Appl. Phys. Lett., 91:224105 (2007).
Melle et al., Structure and dynamics of magnetorheological fluids in rotating magnetic fields, Phys. Rev. E, 61(4):4111-7 (2000).
Merkt et al., Capped Colloids as Light-Mills in Optical Traps, arXiv:cond-mat/0605463v1, pp. 1- 10 (2006).
Metzger, Amorphous Whiskers of a Cobalt-Gold Alloy, Nature, 212:176-7 (1966).
Moller et al., Ultrafine particles cause cytoskeletal dysfunctions in macrophages, Toxicology and Applied Pharmacology, 182(3):197-207 (2002).
National Nosocomial Infections Surveillance System, National Nosocomial Infections Surveillance (NNIS) System Report, data summary from Jan. 1992 through Jun. 2004, issued Oct. 2004, Am. J. Infect. Control., 32(8):470-85 (2004).
Newman et al., Motions of a Magnetic Particle in a Viscous Medium, J. Appl. Phys., 39:5566- 5569 (1968).
Nie et al., Probing Single Molecules and Single Nanoparticles by Surface-Enhanced Raman Scattering, Science, 275(5303):1102-1106 (1997).
Noskin et al., National trends in *Staphylococcus aureus* infection rates: impact on economic burden and mortality over a 6-year period (1998-2003), Clin. Infect. Dis., 45(9):1132-40 (2007).
Nozawa et al., Smart Control of Monodisperse Stober Silica Particles: Effect of Reactant Addition Rate on Growth Process, Langmuir, 21 :1516-23 (2005).
Olsvik et al., Magnetic Separation Techniques in Diagnostic Microbiology, Clinical Microbiology Reviews, 7:43-54 (1994).
Paul et al., Stochastic Dynamics of Nanoscale Mechanical Oscillators Immersed in a Viscous Fluid, Phys. Rev. Lett., 92:235501-1-235501-4 (2004).
Petkus et al., Detection of FITC-Cortisol via Modulated Supraparticle Lighthouses, Anal. Chem., 78:1405-11 (2006).
Puig-de-Morales et al., Measurement of Cell Microrheology by Magnetic Twisting Cytometry with Frequency Domain Demodulation, J. Appl. Physiol., 91:1152-1159 (2001).
Purcell et al., Life at Low Reynolds Number, Am. J. Phys., 45:3-11 (1977).

(56) References Cited

OTHER PUBLICATIONS

Richards-Kortum et al., Quantitative Optical Spectroscopy for Tissue Diagnosis, Annual Review of Physical Chemistry, 47:555-606 (1996).
Rife et al., Design and Performance of Gmr Sensors for the Detection of Magnetic Microbeads in Biosensors, Sensors and Actuators A., 107:209-218 (2003).
Sakoulas et al., Relationship of Mic and bactericidal activity to efficacy of vancomycin for treatment of methicillin-resistant *Staphylococcus aureus* bacteremia, J. Clin. Microbiol., 42(6):2398-402 (2004).
Shankar et al., Experimental Determination of the Kinematic Viscosity of Glycerol-Water Mixtures, Proc. R. Soc. Lond. A., 444:573-581 (1994).
Shelton et al., Nonlinear Motion of Optically Torqued Nanorods, Phys. Rev. E., 71:036204-1-036204-8 (2005).
Shen et al., In situ Detection of Single Micron-Sized Magnetic Beads using Magnetic Tunnel Junction Sensors, Appl. Phys. Letts., 86:253901-1-253901-3 (2005).
Shine et al., The Rotation of a Suspended Axisymmetric Ellipsoid in a Magnetic Field, Rheol. Acta, 26:152-161 (1987).
Spellberg et al., Trends in antimicrobial drug development: implications for the future, Clin. Infect. Dis., 38(9):1279-86 (2004).
Stober et al., Controlled Growth of Monodisperse Silica Spheres in the Micron Size Range, J. Coll. Interface Sci., 26:62-69 (1968).
Su et al., A self-assembled monolayer-based piezoelectric immunosensor for rapid detection of *Escherichia coli* 0157:H7, Biosens. Bioelectron., 19(6):563-74 (2004).
Talbot et al., Bad bugs need drugs: an update on the development pipeline from the Antimicrobial Availability Task Force of the Infectious Diseases Society of America, Clin. Infect. Dis., 42(5):657-68 (2006).
Taylor et al., Real-time molecular and cellular analysis: the new frontier of drug discovery, Current Opinion in Biotechnology, 12(1):75-81 (2001).
Tenover et al., The challenges of emerging infectious diseases. Development and spread of multiply-resistant bacterial pathogens, Jama, 275(4):300-4 (1996).
Tiemersma et al., Methicillin-resistant Staphylococcus aureus in Europe, 1999-2002, Emerg. Infect. dis., 10(9):1627-34 (2004).
Valberg et al., Magnetic particle motions within living cells. Physical theory and techniques, Biophysical Journal, 52(4):537-550 (1987).
Varshney, Interdigitated array microelectrodes based impedance biosensors for detection of bacterial cells, Biosens. Bioelectron., 24(10):2951-60 (2009).
Verbridge et al., High Quality Factor Resonance at Room Temperature with Nanostrings Under High Tensile Stress, J. Appl. Phys., 99:124304-1-124304-8 (2006).
Vignola et al., Effect of Viscous Loss on Mechanical Resonators Designed for Mass Detection, Appl. Phys. Lett., 88:041921-1-041921-3 (2006).
Wagnieres et al., In vivo fluorescence spectroscopy and imaging for oncological applications, Photochemistry and Photobiology, 68(5):603-32 (1998).
Waigh, Microrheology of Complex Fluids, Rep. Prog. Phys., 68:685-742 (2005).
Witte et al., Changing pattern of antibiotic resistance in methicillin-resistant *Staphylococcus aureus* from German hospitals, Infect. Control Hosp. Epidemiol., 22(11):683-6 (2001).
Witte, Antibiotic resistance in gram-positive bacteria: epidemiological aspects, J. Antimicrob. Chemother., 44 Suppl a:1-9 (1999).
Yamazaki et al., Three-Dimensional Analysis of Swimming Properties of a Spiral-Type Magnetic Micro-Machine, Sensors and Actuators A., 105:103-108 (2003).
Yang et al., Interdigitated Array microelectrode-based electrochemical impedance immunosensor for detection of *Escherichia coli* 0157:H7, Anal. Chem., 76(4):1107-13 (2004).
Zhao et al., A Rapid Bioassay for Single Bacterial Cell Quantitation Using Bioconjugated Nanoparticles, PNAS, 101:15027-15032 (2004).

\* cited by examiner

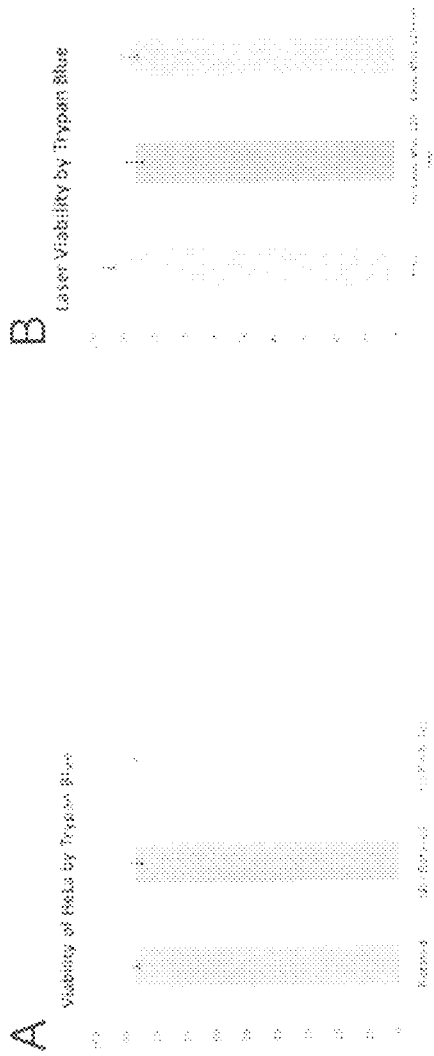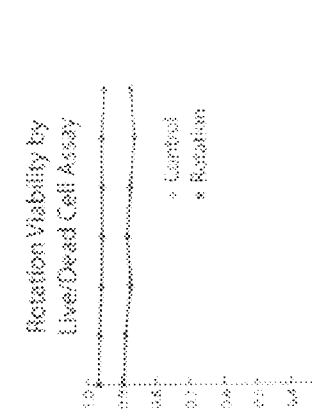
FIG. 3A
FIG. 3B
FIG. 3C

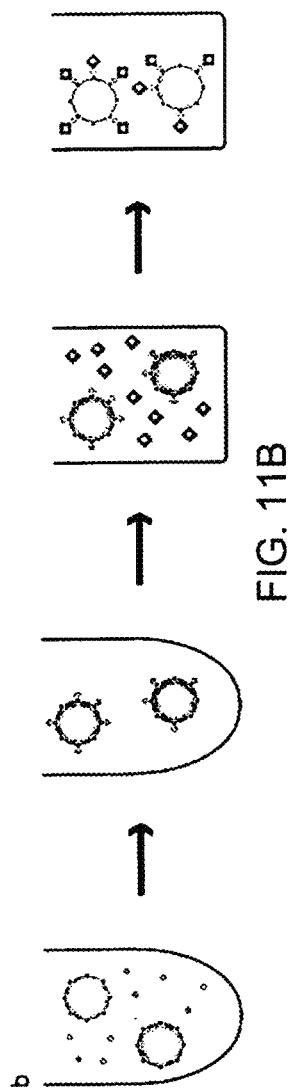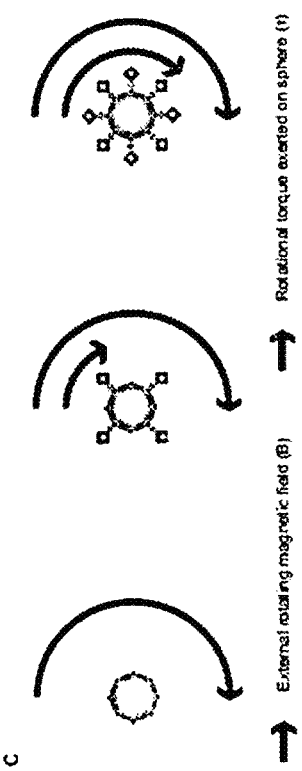
FIG. 11B
FIG. 11C

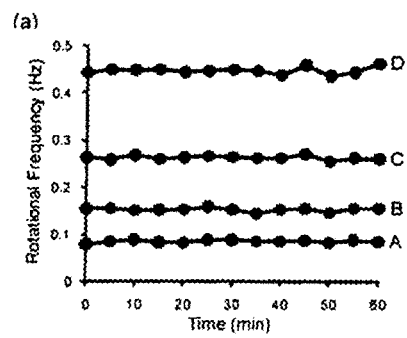 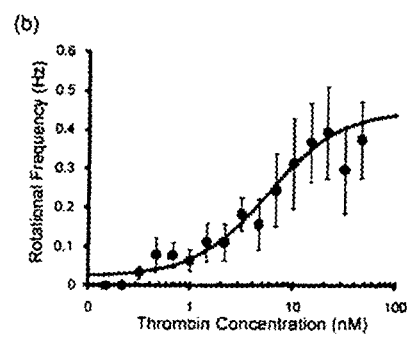
Fig. 19a  Fig. 19b
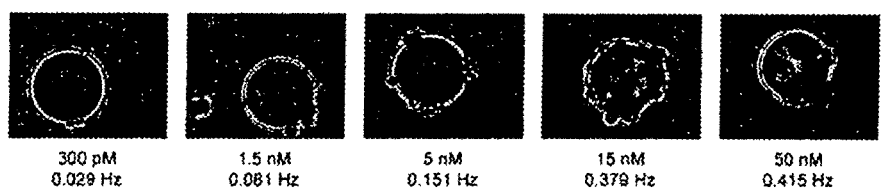
Fig. 20

SEQUENCE LISTING

<160> NUMBER OF SEQ ID NOS: 2

<210> SEQ ID NO 1
<211> LENGTH: 15

-continued

```
<212> TYPE: DNA
<213> ORGANISM: Artificial Sequence
<220> FEATURE:
<223> OTHER INFORMATION: Synthetic primer

<400> SEQUENCE: 1
ggttggtgtg gttgg                                                        15

<210> SEQ ID NO 2
<211> LENGTH: 27
<212> TYPE: DNA
<213> ORGANISM: Artificial Sequence
<220> FEATURE:
<223> OTHER INFORMATION: Synthetic primer

<400> SEQUENCE: 2
gtccgtggta gggcaggttg gggtgac                                           27
```

MAGNETICALLY INDUCED MICROSPINNING FOR SUPER-DETECTION AND SUPER-CHARACTERIZATION OF BIOMARKERS AND LIVE CELLS

CROSS REFERENCE TO RELATED APPLICATIONS

The present disclosure is a U.S. National Phase of International Application No. PCT/US2012/033152 filed Apr. 11, 2012, which claims the benefit of the U.S. Provisional Patent Application No. 61/474,113, filed on Apr. 11, 2011 and U.S. Provisional Patent Application No. 61/474,116, filed on Apr. 11, 2011. The entire disclosure of each application is incorporated herein by reference.

STATEMENT REGARDING FEDERALLY SPONSORED RESEARCH OR DEVELOPMENT

This invention was made with government support under EB009550, RR024986 and CA125297 awarded by the National Institutes of Health and DMR0455330 awarded by the National Science Foundation. The Government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

The invention relates to techniques and devices for quantifying and characterizing analytes and, more particularly, to applying techniques using magnetic rotation of the magnetic particles including internally magnetic analytes.

BACKGROUND OF THE INVENTION

Single cell analysis is necessary to fully capture cell heterogeneity. This may be particularly true for the analysis of cancer cells. A change from two- to three-dimensional environments may radically affect cell behavior, such as gene expression and communication. Currently it is difficult to study the size and shape of freely suspended single cells, particularly Circulating Tumor Cells and disseminating Cancer Stem Cells.

The heterogeneity, i.e., non-uniformity, found in cancer cell populations, and the ubiquitous cell differentiation, has led to increased interest in individual cell studies. Historically, a tumor was thought to originate from the successive divisions of a single 'mother cell', leading to the assumption that all the cells in a tumor shared the same genetic code. However, recent findings have altered this theory, stressing the need for tools that can monitor and track single cells in a high throughput fashion. Currently, standard assays performed on cell populations make individual patterns difficult to access, due to effects of averaging. Flow cytometry, for instance, has been widely used in the last 20 years, for its ability to perform fast analysis on a very high number of cells at a time (e.g., 10,000 cells/s). Time point analysis can also be performed using this technique, but it is not possible to track each cell individually.

It is especially important that a minority of cells, such as stem cells, whose behavior could be considered to be statistically irrelevant compared to the large majority of the population, can have a critical biological and medical impact. For example, the use of the Imatinib drug that targets the BCR-abl fusion protein in patients with chronic myelogenous leukemia (CML) first seemed to be one of the most successful targeted therapies. However, the treatment does not eliminate the CML stem cells, and with the withdrawal of Imatinib the disease reappeared. As a consequence, the focus on cell-to-cell variations has also allowed important breakthroughs in understanding cell differentiation, drug response, protein mechanisms and dynamics, as well as the important role played by stem cells, especially for cancer stem cells. Metastasis relies on cancer cells circulating in the vascular network. The cells responsible for cancer propagation to secondary tumor sites are extremely rare (a few cells per million in the blood), and they go through a circulating stage before populating other tissues. Along with single cell analysis, three dimensional assays also permit a better comprehension of cellular dynamics, by narrowing the gap between in vitro and in vivo behavior. The previously mentioned single cell analysis techniques are all restricted by their confinement of the cell to two dimensions.

Magnetic microbeads have been used in a variety of methods as labels to indicate the presence of a biological molecule. Typically, these assays involve capturing the target of interest (e.g., an antigen or an antibody) on a surface, and using antibody-labeled magnetic beads or particles to bind to the target. The presence of the magnetic labels can be measured in a variety of ways, including changes in magnetoresistance, relaxation time, translational motion, and particle agglutination. Unfortunately, the sensitivity of these methods, as well as their flexibility for use with a variety of analytes, has been limited.

In response, a label-acquired magneto-rotation technique has been developed (referred to as magnetic-label-acquired rotation or MLAR), in which the target facilitates the binding of one or more magnetic labels (e.g., beads) to a nonmagnetic substrate (e.g., sphere) that is typically able to rotate (e.g., floating, suspended, etc.), and the rotational frequency of the resulting sandwich complex in a rotating magnetic field depends on the number of attached magnetic label beads. Label-acquired magnetorotation is derived from asynchronous magnetic bead rotation (AMBR), in which magnetic particles rotate at a different rate than that of a driving magnetic field. AMBR has been used to measure magnetic properties of magnetic particles, dynamic viscosity, detect bacterial cells with single cell sensitivity, and for designing a portable sensor. Asynchronous rotation of microparticles has also been studied in a variety of other systems.

Superparamagnetic beads, which may be micron-sized beads, are typically composed of an inert polymer sphere embedded with superparamagnetic nanoparticles, and may have several advantageous properties for use as labels. The magnetic material of the superparamagnetic beads may be stable over time, and the beads themselves are typically stable over long term storage and under most physiological conditions. Biological samples typically have little, if any, naturally occurring magnetic material, thus reducing the likelihood of background interference (with rare exceptions, such as magnetotactic bacteria). Super-paramagnetic beads may therefore be readily manipulated by external magnetic fields, and can be quantitatively detected by a variety of methods.

Sandwich immunoassays are common assay techniques used to detect biological molecules. A sandwich assay includes three components: a solid phase to isolate the analyte from the solution; the analyte itself; and a label or indicator, which binds specifically to the analyte. This results in the analyte being "sandwiched" between the solid phase and the label. Some of the more frequently used labels include fluorescent molecules and enzymes.

SUMMARY OF THE INVENTION

The present invention provides systems, devices and methods for determining properties from living cells, including mammalian cells, and particularly cancer cells by incorporating one or more magnetic particles into the cell or cells and causing the cell or cells to rotate by applying a rotating magnetic field. Rotation of a cell (or cluster or group of cells) in this manner may be referred to as nanoparticle induced cell magneto-rotation.

Described herein are methods, devices and systems for quantitative, real-time size and morphology monitoring of suspended cells, including suspended live cancer cells. This precision of these methods compares favorably with optical microscopies, with no need for cell confinement to the imaging plane. Single cells are made to acquire a magnetic moment by internalizing magnetic nanoparticles, allowing cell rotation by a magnetic field. The rotational period, monitored in real time, changes with changes in cell morphology. This cell magnetorotation method could be used for multiplexed real time single cell morphology analysis, with possible application to drug testing, drug discovery, genomics and three dimensional culturing.

Specifically, described herein are nanoparticle-induced cell magneto-rotation methods, systems and devices, in which the magnetic field applied and the rotation of the cell are out-of-synch with each other. The cells are first allowed and/or encouraged to incorporate magnetic nanoparticles; the cells are then rotated by applying a rotating external magnetic field of about 1 mT at about 100 Hz. The methods and systems described herein are biocompatible and non-toxic; we note that a thousand-times higher fields, on the order of 1 T, are used for MRI. Further, magnetic nanoparticles have been widely used in biology. The live cell is rotated in suspension, and the rotational frequency is highly sensitive to any morphology change. As reported here, magneto-rotation does not affect the cell's viability, and allows for real time analysis to be performed. Changes in cell morphology are indicated quantitatively by the single cell's rotation period. The trends in the rotation rate allow discrimination between a healthy cell, a dying cell or a swelling cell. In addition, this new technique is easily adaptable to any microscope set-up, is fluorescent-label free, and is compatible with simultaneous fluorescence and/or other optical imaging and spectroscopy methods. Other methods used to track morphological changes of single biological cells include Atomic Force Microscopy (AFM) and Optical Tweezers (OT). These methods may offer higher resolution, but are limited by the attachment of cells to a surface (AFM), or by the irreversible damage caused by laser trapping (OT). In addition, for each cell line, viability studies have to be done for each cell type in order to prevent photodamage, which limits its applicability. The use of cantilevers has also been reported to track the mass of live cells, but there are no publications yet on single cancer cells in suspension.

Nanoparticle induced cell magneto-rotation may be achieved by internalizing functionalized magnetic nanoparticles (fMNPs) into a cell and rotating the entire cell (e.g., mammalian cell) in the presence of a rotating magnetic field. The cell or cells may be rotated in an "asynchronous magnetorotation" manner, in which the cell or cells rotate more slowly than the applied rotating magnetic field. The rate of rotation of the cell (relative to the applied field) is very sensitive to changes in cell volume and shape (e.g. the "effective volume"). As a result, when the cell grows, or dies, which results in a change in cell shape and/or volume, there are significant changes in the asynchronous rotation speed; the rotation typically slows with increasing cell size. In this way, cell growth/death can be rapidly detected and the time and number of cells needed to obtain drug sensitivity results can be dramatically reduced, even to the single cell level.

Because the cells typically incorporate (internalize) the magnetic particle or particles, they may also be separated or enriched by applying a magnetic field, including a static magnetic field either before, during or after the application of the rotating magnetic field. For example, an important step in chemosensitivity testing is the enrichment and isolation of the cells of interest. Indeed, fMNPs have been widely used for immunomagnetic separation of cancer cells in research settings, used for isolation of stem cells and in clinical settings, and also used for separation of circulating tumor cells (CTCs). fMNPs are FDA approved for this purpose. The approach described herein may allow the integration of immunomagnetic separation for sample enrichment with cell magneto-rotation techniques for monitoring cell growth/death described herein. By combining immunomagnetic separation/enrichment with the Cell Magnetorotation methods described herein, reliable drug sensitivity assays with single cell accuracy can be performed clinically.

The magneto-rotation of single cancer cells described herein may allow the measurement of changes in cells in suspension (without attachment), allowing the study of cells that are in suspension in vivo, such as Circulating Tumor Cells (CTCs) among others.

In general, the cells may be allowed or induced to internalize one or more magnetic particles. These particles may be coated or embedded (or may otherwise include) one or more linking/binding sites which may secure the magnetic particle to the cell surface and/or to an internal structure within the cell. In some variations the cells are exposed to the magnetic particles which may bind to the cell surface (e.g., via integrins or other cell-surface binding) and become internalized (e.g., endocytosis) into the cell. In some variations the cells may be injected or otherwise treated so that magnetic particles are internalized. Once internalized the magnetic particles may be secured (e.g., bound, linked, cross-linked, etc.) to the cell so that the magnetic moments of the internalized particles are summed to rotate the cell. Thus, the internalization of magnetic nanoparticles makes the cell its own, self-calibrating actuator. This method is distinguished from other methods involving the binding or attachment of cells to one or more magnetic particles that remain outside of the cell, which may include magnetic particles that are larger or approximately the same size as the cell. Such methods may be disadvantageous because they may rely on external beads that put constrain on the cell's membrane and confuse the cell's signaling; in the methods described herein, the internalized nanoparticles are typically inert, allowing cell-cell interaction while rotating.

In addition, the internalization of magnetic nanoparticles may allow surface treatments of the cell without modifying the magnetic content of the cell, which would not be possible with particles (micro or nanoparticles) attached externally to the cell (e.g., the outer membrane of the cell). The apparent fluid flow created at the surface of the cell could help mimic the environmental conditions of a circulating cell.

In some variations, the cells may be aggregated or allowed to aggregate. Cells may naturally aggregate (e.g., forming clusters or spheroids), or they may be induced to aggregate because of the magnetic properties (e.g., clustering because of their internalized magnetic particles). Once aggregated, it may be beneficial to apply the rotating magnetic field to induce magneto-rotation of the multi-cellular aggregates to observe properties (e.g., growth/death, response to drugs, etc.). For example, in one variation, magneto-rotation of a group of single cells and the formation and rotation of magnetic spheroids may be used to study micro-tumors. Growth, Chemosensitivity and/or radiation therapy assays can be studied this way.

In some variations, the methods described herein may also be used to create or take tomographic reconstructions of cells or cell aggregates. For example, a cell or cell aggregate that has taken up magnetic particles as described herein, may be rotated to numerous angles of it. A 3-dimensional reconstruction could then be made using these images. For example, after introducing magnetic material to a spheroid formed by cancer cells, one can rotate the spheroid by introducing a rotating magnetic field. In this manner, the spheroid can be imaged from all angles using a microscope or other imaging instrument, and a 3-dimensional reconstruction can be made. Single cells can also be rotated in the same manner for imaging. Other microscopic entities can also be rotated in the same manner, after introducing magnetic moment by specific or nonspecific interactions.

Also described herein, the present invention provides methods, systems, and devices for measuring and/or characterizing an analyte using magnetic-label-acquired rotation. Any appropriate analyte may be examined using this technique, including proteins, nucleotides, cells, non-biologics (e.g., particles, nanostrucutres, etc.), or the like.

In general, magnetic-label-acquired rotation (MLAR) includes a substrate (which may be a spherical substrate) that binds to an analyte, and a magnetic label that also binds to the analyte (typically in a different, non-competitive location); the intensity of the magnetic label bound (and therefore the amount of analyte binding, and in some variations thus the amount of analyte) may be determined by the rate of rotation of the substrate in a rotating magnetic field.

For example, MLAR may consist of the following components: mother spheres (substrate), daughter spheres (magnetic label), affinity molecules and a platform; the affinity molecules may bind a target such as an analyte. The mother spheres are typically larger than daughter spheres, and are also usually nonmagnetic. For example, mother spheres may be of any appropriate size, for example, the range from 5-100 μm in diameter. Daughter spheres are typically smaller than mother spheres and are magnetic (either paramagnetic, superparamagnetic or ferromagnetic). For example, daughter spheres may be of any appropriate size, for example, the range from 0.01-5 μm in diameter. As mentioned above, targets may be any appropriate analyte, including proteins, biomarkers, or any other molecule of biological origin (or non-biological origin) which is intended to bedetected or measured. Affinity molecules may include molecules that are attached or linked to the mother spheres and daughter spheres to bind to the target. Affinity molecules could include antibodies, aptamers, ligands, or other affinity molecules that exhibit preferential binding to the target. In some variations the affinity molecules may non-specifically bind. In some variations one or more adapter of linker molecules (e.g., connecting a target-binding molecule to the mother or daughter sphere (substrate and label) may be used). In one variation, affinity molecules could form a sandwich pair where the two affinity molecules bind to different sites on the target molecule and therefore "sandwich" the target; one of the types of affinity molecules would be attached to the mother spheres, and one would be attached to the daughter spheres.

In some variations the system includes a platform, e.g., an apparatus in which MLAR is performed. This platform may include a chamber (e.g., glass coverslips, a microfluidic chip made from glass, poly(dimethy siloxane), silica or other material, etc.) through which the sample including the target bound to substrate and magnetic label can be visualized. The platform may also be configured to be surrounded by a two-dimensional rotating magnetic field. Any appropriate visualization method or sub-system may be used to determine rotation of the "sandwich" formed by the substrate (e.g., mother sphere), target and magnetic label (e.g., daughter sphere).

In some operational variations, MLAR includes the steps of attaching a target-specific affinity molecules to the substrate (e.g., mother spheres) and the same or different target-specific affinity molecules to the magnetic label (e.g., daughter spheres). For example, the substrate would then be incubated with a solution that (possibly) contains the target. After incubation with the target, the daughter spheres may be introduced, and the affinity molecules on the surface of the daughter spheres may bind to the target that is bound to the affinity molecules on the surface of the mother sphere. Thus, magnetic beads may effectively be attached to the surface of the nonmagnetic mother spheres in an amount that reflects the concentration and/or conformation of the target molecule. The number of attached daughter beads may therefore be a function of the number of target molecules bound to the mother sphere, which would be a function of the concentration of target present in the solution in which the mother spheres were incubated. The collective attachment of magnetic label (e.g., daughter spheres) to a substrate (e.g., mother sphere) may be termed a "sandwich complex." When placed in a rotating magnetic field, the rotational frequency of the sandwich complex is a function of the number of attached magnetic beads. Therefore, the rotational frequency of the sandwich complex can be correlated to the number of attached magnetic beads. Although the substrate is exemplified and described as a mother sphere herein, any appropriate substrate (including non-spherical substrates) may be used. Substrates that may be rotated are particularly desirable, including substrates that may be suspended in a solution (e.g., aqueous solution) so that they are free to move. Similarly, any appropriate magnetic label may be used, although the label described herein are referred to and exemplified as "daughter spheres". Non-spherical magnetic labels may also be used. Small (e.g., nanoscale, including <100 nM in diameter) magnetic labels may be used.

Monitoring and/or detection of analytes using MLAR may be particularly useful in circumstance when it would be beneficial to measure without the use of florescence. As mentioned, virtually any analyte may be monitored or measured by MLAR. For example, MLAR may be used to measure antigens associated with infection diseases, biomarkers associated with cardiac distress, and biomarkers associated with cancer growth and development.

In general, detection of the level of magnetic label (and therefore the level of binding to antigen) may be determined by rotating the sandwich in a rotating magnetic field. A rotating magnetic field (e.g., rotating at 100 Hz) will cause rotation of the substrate (e.g., mother bead) because of the presence of the magnetic labels attached via the analyte. In general, the more magnetic label (and therefore the more analyte), the faster the sandwich will rotate in the presence of the rotating magnetic field. The rotating may be analyzed (and/or visualized) using any appropriate manner. For example, MLAR can be observed under a microscope or by shining a laser on the sandwich complex and extracting the rotational frequency from the resulting rotating lightpattern.

The disclosure provides a method of detecting a target, comprising contacting the target with a plurality of magnetic particles under conditions under which the magnetic particles are capable of associating with the target, applying a rotating magnetic field to the target, and detecting rotation in the magnetic field arising from association of one or more magnetic particles in the plurality associated with the target, wherein detection of rotation of the target indicates presence of the target.

In some aspects, the target is a target cell, and in further aspects a change in the rotation of the target cell over time indicates growth of the target cell. Association as described herein is effected by one or more of the particles being internalized by the cell. In some aspects, the particles are internalized in a non-specific manner, and in further aspects one or more of the magnetic particles comprises a targeting moiety and association is effected by binding of the one or more magnetic particles to the target. A targeting moiety, as described herein, is in various aspects a peptide, an antibody, a nucleic acid, an aptamer or a combination thereof.

Methods disclosed herein include those wherein particles associated with the cell induce rotation of the cell.

The disclosure also provides aspects wherein the target cell is in a population of target cells. In related aspects, the population of target cells is an aggregate of cells. Thus, in various aspects, the target cell is present within a population of cells, while in further aspects the population of cells comprises a plurality of target cells that are in an aggregate.

In still further aspects, the population of target cells contain target cells of different morphology. It is therefore further contemplated by the disclosure that, in some aspects, the population of target cells rotate at different rotation rates based on the different morphologies. The different morphology is, in some aspects, a cellular deformation which includes without limitation a cell surface protrusion and/or is due to a genetic or biochemical change within one or more cells of the population.

The disclosure further contemplates that any type of cell may be utilized in the methods provided herein. In some aspects, the target cell is a cancer cell. Cancer cells useful in the practice of the methods described herein derive from tissues including, without limitation, heart, liver, pancreas, prostate, brain, eye, thyroid, pituitary, parotid, skin, spleen, stomach, esophagus, gall bladder, small bowel, bile duct, appendix, colon, rectum, breast, bladder, kidney, ureter and lung.

In further aspects of the disclosure, the target is an analyte. It is contemplated that, in various aspects, the analyte is a biological analyte and/or a non-biological analyte.

In aspects wherein the analyte is biological, it is further contemplated that the biological analyte is a protein or a nucleic acid. In one aspect, the analyte is thrombin.

In those aspects that include a non-biological analyte, the disclosure provides that in some aspects the non-biological analyte is a metal.

Methods provided herein also include those wherein the target is immobilized on a substrate. In some aspects, the substrate is a substrate particle, and in further aspects the substrate particle is not magnetic.

It is also contemplated by the disclosure that, in some aspects, one or more magnetic particles and/or the substrate particle comprise a binding agent. Thus, binding agents are also provided in the disclosure and include, without limitation, an antibody, an aptamer, a peptide, a ligand or a combination thereof. Further aspects thus include those wherein the target is specifically bound by the binding agent.

The disclosure further provides aspects wherein the magnetic particles and/or the substrate particle bind the target to form a complex between the particle, the target and the substrate particle. In additional embodiments of the disclosure, methods are provided that further comprise determining a rate of rotation of the complex to determine concentration of the analyte, wherein rotation of the complex when the analyte is present is different than rotation of the complex when the analyte is absent. In related aspects of these embodiments, a higher concentration of analyte in the sample produces a faster rotation of the complex relative to a lower concentration of analyte in a control sample.

In another embodiment of the disclosure, a method of determining sensitivity of a first population of cells to a drug is provided, comprising contacting a plurality of populations of cells with a plurality of magnetic particles under conditions under which the magnetic particles are capable of associating with the populations of cells, contacting the populations of cells with the drug, and applying the external rotating magnetic field to the populations of cells to determine a rotation of each population of cells, wherein a difference in rotation of the first population of cells compared to rotation of a different population of cells is indicative of the sensitivity of the first population of cells to the drug. With respect to sensitivity, the disclosure contemplates that in various aspects the sensitivity is increased sensitivity. As described herein, and in further aspects, the difference in rotation is due to a morphological deformation. The morphological deformation is, in various aspects, a cell surface protrusion or is due to a genetic or biochemical change within the cell.

In some aspects, the first population of cells is an aggregate.

In yet another embodiment, the disclosure provides a method of rendering a non-magnetic target magnetic comprising the step of contacting the target with a magnetic particle under conditions under which the magnetic particle is capable of associating with the target, wherein association of the magnetic particle with the target enables magnetic field induced rotation of the target. The target, in various aspects, is a target cell, and in further aspects contacting the target cell with the magnetic particle comprises associating the magnetic particle internal to the target cell.

It is further provided that any of the methods described herein is performed in a multiplex fashion.

BRIEF DESCRIPTION OF THE DRAWINGS

FIG. 2 illustrates changes in the rotation period of a single HeLa cell in.

FIG. 3A illustrates HeLa cells viability after incubation with nanoparticles and rotation under a rotating magnetic field. All the cells came from the same cell line, and were cultured at the same time, each for 4 days. HeLa cells were grown until reaching 70% confluency, and the first sample constituted the control group (RHS). The two other groups, incubated with magnetic nanoparticles, originated from the same cell batch, cells grown in the presence of 40 ug/ml in DMEM, until reaching 70% confluency. Each group was made of two samples containing 50,000 cells each. While the second sample was not rotated, the third one (control) was put under a field of 0.5 mT and rotated at a driving frequency of 100 Hz (LHS). During the experiment, cells were maintained at 37° C., with 5% $CO_2$ and humidity control. For every group, n=3. Values represent mean+/−s.d. All the cells came from the same cell line, and were cultured at the same time, each for 4 days. HeLa cells were grown until reaching 70% confluency, and the first sample constituted the control group (RHS). The two other groups, incubated with magnetic nanoparticles, originated from the same cell batch, cells grown in the presence of 40 ug/ml in DMEM, until reaching 70% confluency. Each group was made of two samples containing 50,000 cells each. While the second sample was not rotated, the third one (control) was put under a field of 0.5 mT and rotated at a driving frequency of 100 Hz (LHS). During the experiment, cells were maintained at 37° C., with 5% $CO_2$ and humidity control. For every group, n=3. Values represent mean+/−s.d.

FIG. 3B shows magnetic HeLa cells viability before and after laser exposure. HeLa cells were incubated with magnetic nanoparticles, for 48 hours, following the protocol described before. In a 96-well plate, 150 ul of each set of cells was pipetted. Control measurement (blue) was realized after cells were washed, detached and resuspended in fresh media at 37° C. Non-exposed (red) and exposed cells (green) were kept on the microscope stage for 120 min at room temperature. Each well contained 25,000 cells. Values represent mean+/−0.5*s.d. n=3.

FIG. 3C illustrates HeLa cells viability during magneto-rotation at 37° C., with humidity and 5% CO2 control. HeLa cells were pipetted onto a Live Cell Array (NUNC™) The cells trapped in the 100 um wells were counted using Calcein. For both the control and the rotated cells groups, n=4. Cell death was monitored using Propidium Iodide. Standard deviations are within the dots.

In FIG. 7A, the spheroid is about 100 µm wide, and are made of a few dozens of cells, while in FIG. 7B the spheroid is made of more than a thousand cells (it is also wide enough to be visible without a microscope, at least 500 um).

(FIG. 8A) Fluorescence Image (40×) of a HeLa cells after incubation with dyed magnetic nanoparticles at an extracellular iron concentration of [Fe]=12.5 ug/ml (0.22 mM). (FIG. 8B) Cellular iron content in picogram per cell. The concentrations of particles in the media are given in iron concentration (error bars values represent mean+/−0.5*s.d., n=3)

FIGS. 11a and 11b show a schematic representation of the design of label-acquired magnetorotation. FIG. 11a shows three components of a sandwich assay, including a solid phase sphere (6.7 µm streptavidin-coated sphere), an analyte mimic (40 nm biotin-coated particle), and a label (1 µm streptavidin-coated superparamagnetic bead). Streptavidin is a 60 kDa tetrameric protein, and is represented by the cloverleaf symbol in the schematic representation. Biotin is a 244 Da molecule, and is represented by blue dots. FIG. 1b illustrates the steps including initially incubating the analyte with the spheres in a microcentrifuge tube. Following removal of the unbound analyte, the solution is transferred to a square-bottom 384-well plate, where the spheres are incubated with magnetic beads that bind selectively to the analyte, which forms a sandwich complex. FIG. 11c illustrates the method of detection by applying a rotating magnetic field. In the presence of a rotating magnetic field of constant magnitude, the rotational frequency of the "sandwich" is a function of the number of attached superparamagnetic label beads.

FIG. 14a illustrates a frame-by-frame analysis of four different rotating sandwich complexes. The angle at each time point represents the number of degrees through which the complex has rotated since $t_0$ (360 represents one full rotation). The rotational frequency of the complex is shown above each trace. FIG. 14b shows ten frames from each of the videos taken for FIG. 14a in 0.5 second intervals. The top sandwich complex completes about 1.75 rotations over the 10 frames, while the bottom sandwich complex completes about 0.75 rotations over the 10 frames. The driving frequency is 20 Hz for all samples. Scale bar is 5 μm.

FIG. 19a illustrates the plots of rotational frequency of four sandwich complexes measured every five minutes over the course of an hour. The rotational frequency means, ±SD (CV %) of the four sandwich complexes (A-D) are 0.0856±0.0028 Hz (3.3%), 0.1523±0.0038 Hz (2.5%), 0.263±0.0040 Hz (1.5%) and 0.448±0.0073 Hz (1.6%), respectively. This demonstrates that the rotation of the sandwich complexes is stable over time. FIG. 19b illustrates a dose-response curve for the detection of thrombin by LAM. The data are fit by a four-parameter logistic equation ($r^2=0.971$). Each data point represents the average±SD of 15 sandwich complexes.

FIG. 20 are screenshots of five sandwich complexes taken through a 100× oil-immersion objective. The thrombin concentration and the rotational frequency of each complex is shown below the picture. The number of magnetic beads on and the rotational frequency of each sandwich complex appears to increase with concentration of thrombin.

DETAILED DESCRIPTION

In general, a cell may be allowed or induced (or treated) to internalize one or a plurality of magnetic particles. As mentioned above, the magnetic particles may be functionalized by including one or more agents (e.g., proteins, nucleotides, active groups, functional groups, etc.) that allow the attachment and/or internalization of the magnetic particles within the cell. In some variations the cell or cells are injected with the magnetic particles; in some variations the cells are co-incubated with the magnetic particles and internalized by cellular mechanisms (e.g., endocytosis, etc.). In some variations the cell(s) is/are permiablized or made permeable to the magnetic particle(s) which may be retained within the cells by binding or to an internal structure within the cell(s). Any appropriate cell may be treated and observed as described herein, including but not limited to mammalian cells, eukaryotic cells generally prokaryotic cells, etc. For example, the cells may be bacteria, yeast, etc. Incorporation of the magnetic beads may be performed in any appropriate manner, including co-incubation and cross-linking of the magnetic beads to the surface of the cell (e.g., to a cell-surface protein, etc.), which may trigger internalization of the magnetic particles. Thus, in general, the magnetic particle may be sized so that one or a plurality of particles may be internalized without harming the cell.

Example—Magnetic Rotation of Cells Via Internalized Magnetic Particles

Figure 1A:
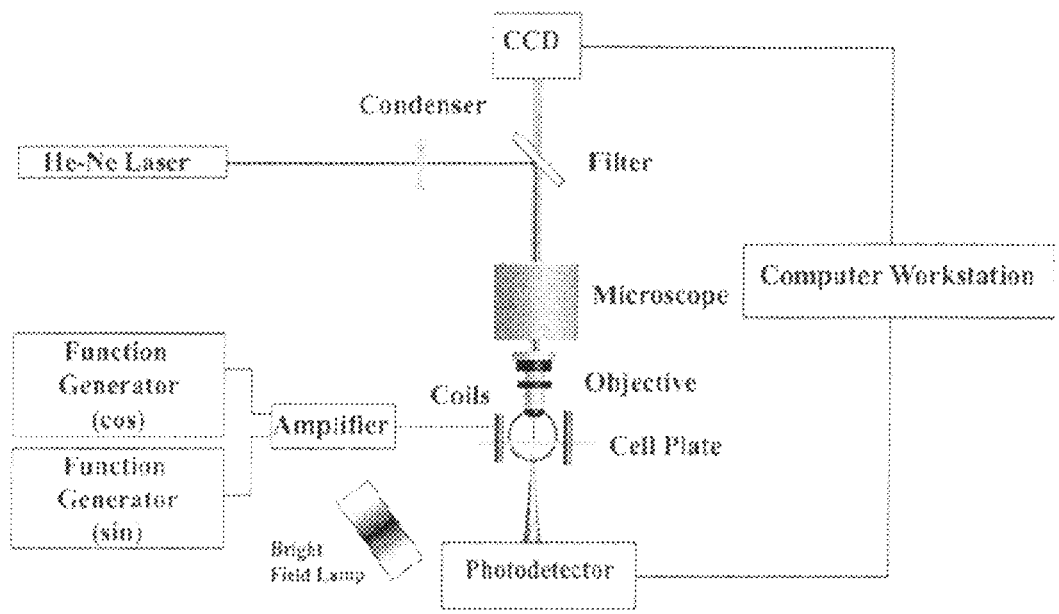
FIG. 1A illustrates a schematic of an example implementation in accordance with the present application. In this example, a LIVE CELL ARRAY plate, with 100 μm wells, is placed on the platform of a microscope, for which a set of electromagnetics has been adapted. Note that the cell is not stuck to the bottom of the well. Under the 60× objective, the laser beam undergoes forward scattering from the rotating cell (15 to 20 µm), and the variations in the forward scattered light is captured in real-time by a photo-detector, and analyzed on a computer.
Figure 1B:
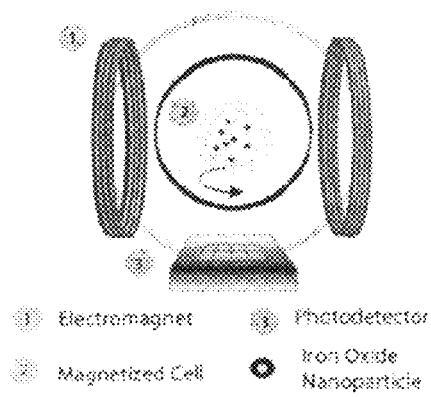
FIG. 1B shows a schematic of a rotating cell placed inside the magnetic coils: two identical sinusoidal signals, with a phase shift of 90°, pass through the two pairs of coils. The applied magnetic field and the magnetic moment of the cell are not aligned, creating a torque that drives the cell's rotation.
Figure 1C:
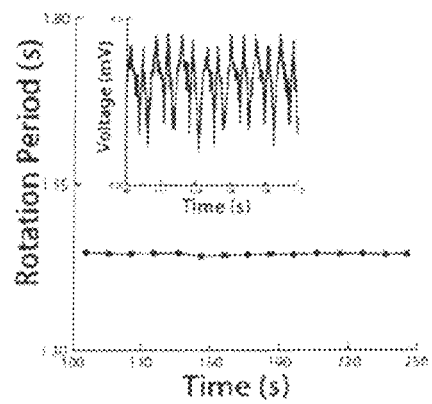
FIG. 1C illustrates a rotational period of a fixated cell in DMEM. The inset represents the raw signal from the photodetector, showing the periodicity over a given time window. The treatment of the signal then gives the rotational period.

A schematic of one variation of a system for rotating cells that have internalized magnetic particles is shown in FIG. 1A. To verify that cells could be magnetically manipulated, we placed them in the center of magnetic coils with magnetic field amplitudes of 1 mT, as shown in FIG. 1B. The coils in this example have been adapted to the platform of a microscope to record videos. The single cells may rotate at frequencies ranging from 0.05 Hz to 2 Hz in this setup (much lower than the 100 Hz driving fields, due to operating in the asynchronous regime, described in greater detail below). Focusing a low power, 1.45 mW HeNe laser through the microscope, the forward scattered signal is recorded with a photodiode. The cell viability is not affected by this low-intensity laser. When the cell rotates, it produces rotational-dependent modulation that can be measured with the photodiode. With real-time signal processing, the rotation period of the cell and therefore its size, can be monitored in real-time.

The cell in this example is found to exhibit magnetic rotational behavior very similar to that of a magnetic microparticle. In the asynchronous regime, with superparamagnetic particles, the mean value of the rotation speed of the single cell is given by:

$$\left(\frac{d\theta}{dt}\right) = \frac{\text{Torque}}{\text{Drag}} = \frac{\Gamma}{\kappa \eta V}$$

where $\Gamma$ is the magnetic torque and $\kappa \eta V$ is the drag due to viscosity forces. Here, $\kappa$ is its Einstein's shape factor, V is the volume and $\eta$ is the coefficient of viscosity. We note that $\Gamma$ is proportional to the magnitude of the magnetic field, the magnetic moment of the cell and the volume of the magnetic contents of the cell; however, all these parameters are kept constant in the experiments. Therefore, in the asynchronous regime, any change in the cell's shape or volume, i.e., in its effective volume, $V_{\it eff} = \kappa K$, induces a change in the critical frequency (everything else being equal), and, consequently, in the rotation speed, given by the above formula. This model has been further refined for the case of paramagnetic particles, wherein the rotational period, T, is found to be proportional to the effective volume, $T \propto V_{\it eff}$, where the effective volume is again $V_{\it eff} = \kappa V$ (this is true in the asynchronous rotational regime). As can be seen from this dependence, if the volume increases, the rotation period increases proportionally. The same goes for the shape factor, and, as a consequence, one can detect morphology changes.

In this example, cancer cells loaded with nanoparticles were magnetically separated and resuspended in different media, such as culture medium (DMEM), DMEM with 5% Ethanol, or DMEM with 75% deionized water. Each medium was used to verify different aspects of this method: DMEM was used as a control, ethanol was used as a cytotoxic agent, and, to promote stress through cell swelling, we used a large proportion of DI water, reversing the ionic balance between the inside and outside of the cell. Note that a large concentration of salt in solution has the opposite effect on the cell, namely shrinking it. The cells in suspension were then pipetted onto a LIVE CELL ARRAY plate (NUNC), where the array has 100 µm wide wells, which provide adequate compartments for single cells to rotate and be analyzed. Optical scattering signals were recorded and the changes in the rotation period were measured for the different media (FIG. 2).

Figure 2A:
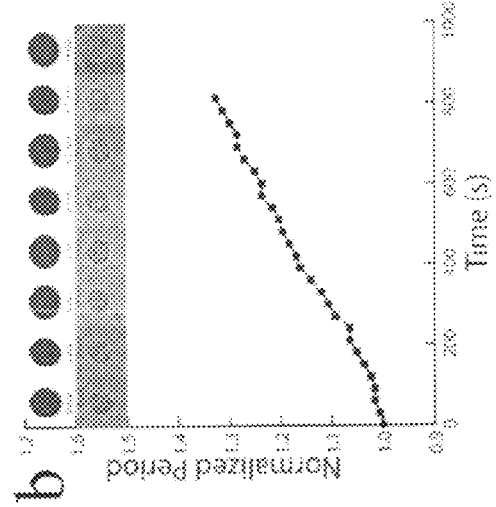
(FIG. 2a) In DMEM on an agarose layer (FIG. 2b) In a mixture of 75% DI water and 25% DMEM (FIG. 2c) In a mixture of DMEM with 5% Ethanol and (FIG. 2d) for a live cell in DMEM (green circles) compared to a HeLa cell (red squares) in DMEM with a 100 ug/ml of Cisplatin. The Y axis is the normalized period, and the X axis is time in seconds. Lines show trend between connected points. For each graph, in the pictures above it, the bottom pictures show snapshots of the rotated cell at each indicated time, while the schematic pictures on top of it show the corresponding cell shapes (fixated cell not shown). Dark discs represent the cell cytoplasm and membrane, while grey spots show the vesicles formed at the surface, if any.
Figure 2B:
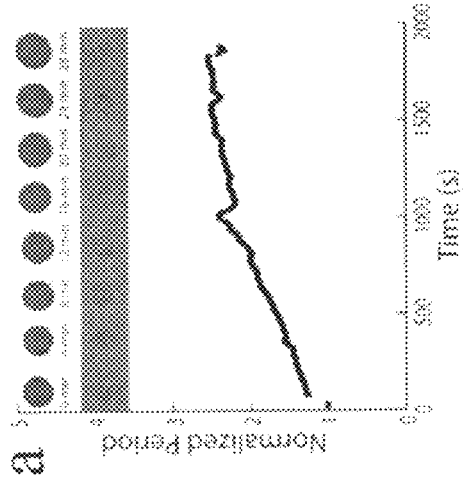
Figure 2C:
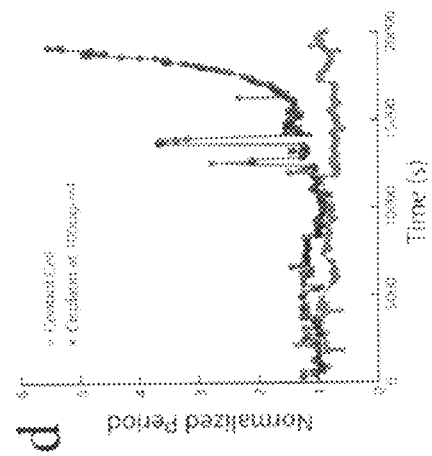
Figure 2D:
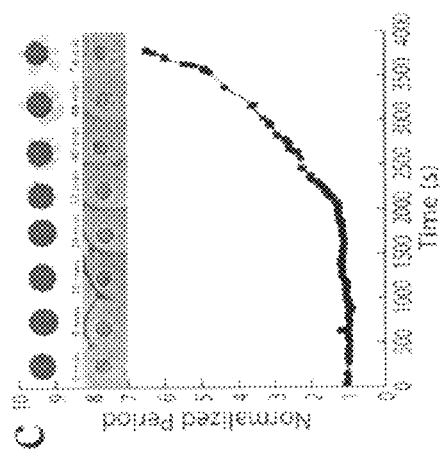
Figure 5:
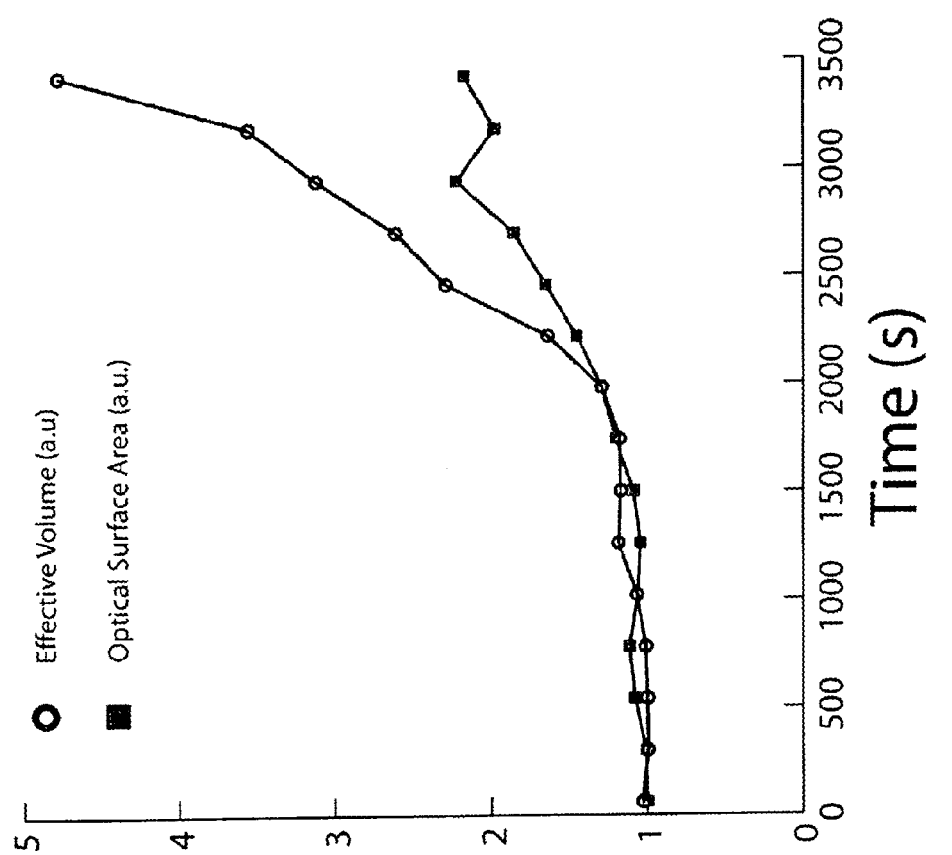
FIG. 5 shows a comparison of sensitivities between a microscope and magneto-rotation in measuring cell death (HeLa cell in DMEM, 5% Ethanol). The line with boxes is the normalized surface area as measured with the microscope, and line with circles is the normalized effective volume period as measured with Magneto-Rotation.

FIGS. 2A and 2B show two cases of cell swelling. Cell swelling generally occurs because of the osmotic pressure created either by an ionic imbalance, as mentioned earlier, or by a lack of nutrients. Either way, the cell expands to cope with the imbalance of the chemicals it needs for maintaining its metabolism. To reach ionic disparity, we used DI water (FIG. 2B). We also observed that cells would also swell when placed on an agarose layer (2% agarose in DI water) (FIG. 2B). Agarose gel is porous, a property that is used in the electrophoresis of proteins, and this property might be at the origin of the swelling. Indeed, the nutrients present in the growth media, mainly glucose, can diffuse into the agarose gel while the cells rotate above it. The cells would therefore swell to balance the reduced concentration of nutrients available in solution, as observed by Goldberg et al. in cortical cells. Since the cell volume increases, the rotation period increases. Alternatively, cell death is provoked when placed in a solution with 5% ethanol (FIG. 2C) or using a concentration of 100 ug/ml of Cisplatin in solution (FIG. 2D, red line connecting squared dots). However, the mechanisms of these kinds of cell deaths are different from the cases above, since blebs appear at the surface of the cell. In 5% ethanol, it takes only around 30 minutes (FIG. 2C) for blebs to appear, while in the case of the treatment by Cisplatin at 100 ug/ml, it takes several hours. Contrary to the swelling case, it is the changes in shape of the cell membrane that increase the effective volume. Blebbing and the formation of vesicles at the surface of the cell indicate that the cell contents are being broken down and separated into several vesicles. As the death process continues, the vesicle sizes increase. This kind of phenomenon does not only add to the volume, but it critically affects the shape factor of the cell. The combination of these two parameters, namely the effective volume, is what is tracked with magnetorotation, thus amplifying the blebbing effect. Eventually, the drag on the cell becomes so high, compared to the initial state of the cell, that the cell rotation period rises drastically (by 550%), in a non-linear way (see FIG. 2C, red line on FIG. 2D and see FIG. 5 for a comparison with microscope measurements). Thus both cell death mechanisms, though very different, can be observed and differentiated with Cell Magnetorotation.

We also performed magnetorotation of a healthy cell (FIG. 2D, line with open circles), in growth media. In the absence of a toxic agent, the rotation period did not significantly change (the standard deviation of the rotation period was 3.07%). A fixed morphology control test was realized by fixating the cells in a 4% formaldehyde vial (1.5 ml) for 10 min, under end-over-end vial rotation (FIG. 2D, line with squares). Since the membrane and the cell contents were cross-linked, the cell morphology did not change, under isotonic conditions, and thus, as expected, the rotation period did not change. As compared to a fixated cell, where the rotational period is very flat, for live cells we observe that the rotation period, over time, exhibits larger short-time fluctuations. This may be a result of the cell metabolism, which is still active during rotation. Overall this shows that when the rotation period is constant, it corresponds to a cell that is not significantly changing in its effective volume.

To investigate the ability of the setup to monitor cell death, without causing cell death, we conducted several viability tests (laser exposure, short term and long term effects of rotation on viability, cell division and clonogenicity).

We first tested the effect of the uptake of magnetic nanoparticles [yellow (RHS) and red (middle) bars in FIG. 3A], and of the presence of a magnetic field, on cell viability [red (middle) and blue (LHS) bars in FIG. 3A]. We performed the viability test on three different HeLa cell populations. After an hour at 37° C., with humidity and $CO_2$ control, a cell count was made using Trypan blue. There was no significant difference in viability among the three cell groups (FIG. 3A). This shows that neither the incorporation of the particles nor the rotation under a magnetic field affected the cells viability over the time scale of an hour. Indeed, the same kind of magnetic iron oxide nanoparticles are quite commonly used to magnetophoretically separate certain cell populations from heterogeneous populations, as well as during MRI scans on patients (for contrast enhancement), without causing harm to cells. In the above viability tests, the field intensity and the magnetic particle concentrations were purposely set at higher values (0.5 mT and 40 ug/ml) than those described in this paper for magnetorotation (0.1 mT and 25 ug/ml), in order to keep a safety margin in the protocol.

Another possible concern we addressed is the effect of the laser exposure on the cell's viability (FIG. 3B). The viability test shows no significant cell death and no significant difference after two hours, between control cells and magnetic cells that were exposed to the laser. Both the interaction of the cells with light and the possible interaction of the magnetic nanoparticles with the laser do not affect the viability of the cells.

Figure 9:
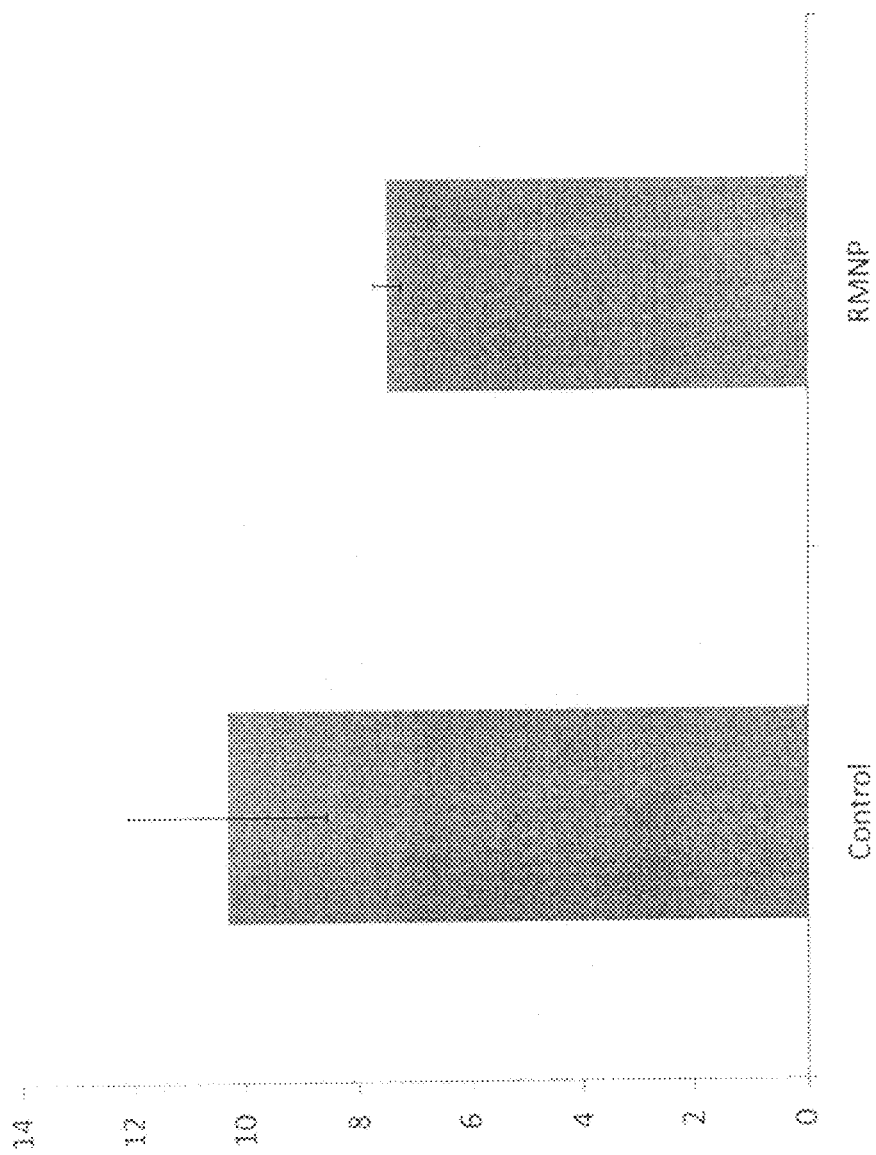
FIG. 9 shows a clonogenic assay on HeLa cells incubated with magnetic nanoparticles (12.5 ug/ml, unfiltered) and rotated for 24 hrs in an incubator. For each sample, after incubation with magnetic nanoparticles following the standard protocol, cells were washed, detached and counted. 10000 cells were then rotated for 24 hrs at 37° C., in a 5% CO2 environment with humidity control. Using a 6-well plate, 200 cells were put to grow on an agarose layer (1.3% agarose in DMEM) for 3 weeks. Control cells were not exposed to nanoparticles nor to any magnetic field. Control cells were washed, detached, counted and for each well, 200 cells were put to grow on agarose. Values represent mean+/−0.5*s.d. n=3.

Finally, we investigated the possible impact of the physical rotation of the cells on their viability. Indeed, in order to accurately monitor toxicity effects, cell rotation has to be harmless. FIG. 3C addresses this latter point. Comparing the death rate of rotating cells and the death rate of non-magnetic cells, we found no statistical difference in the two trends (n=4, p=0.245>0.05, F=1.65<5.98=$F_{crit}$). In addition, as we observed (data not shown) and as described in other publications, cells containing magnetic nanoparticles can be subcultured. Also, to assess the cells' clonogenicity, we performed a clonogenic assay where cells were first magnetically rotated for 24 hours in an incubator, and then let to grow on agarose for three weeks. We found no significant difference between the control samples and the rotated samples (n=3, t=1.37<2.77=$t_{crit}$, 0.24>0.05=$p_{crit}$, see FIG. 9).

Figure 10:
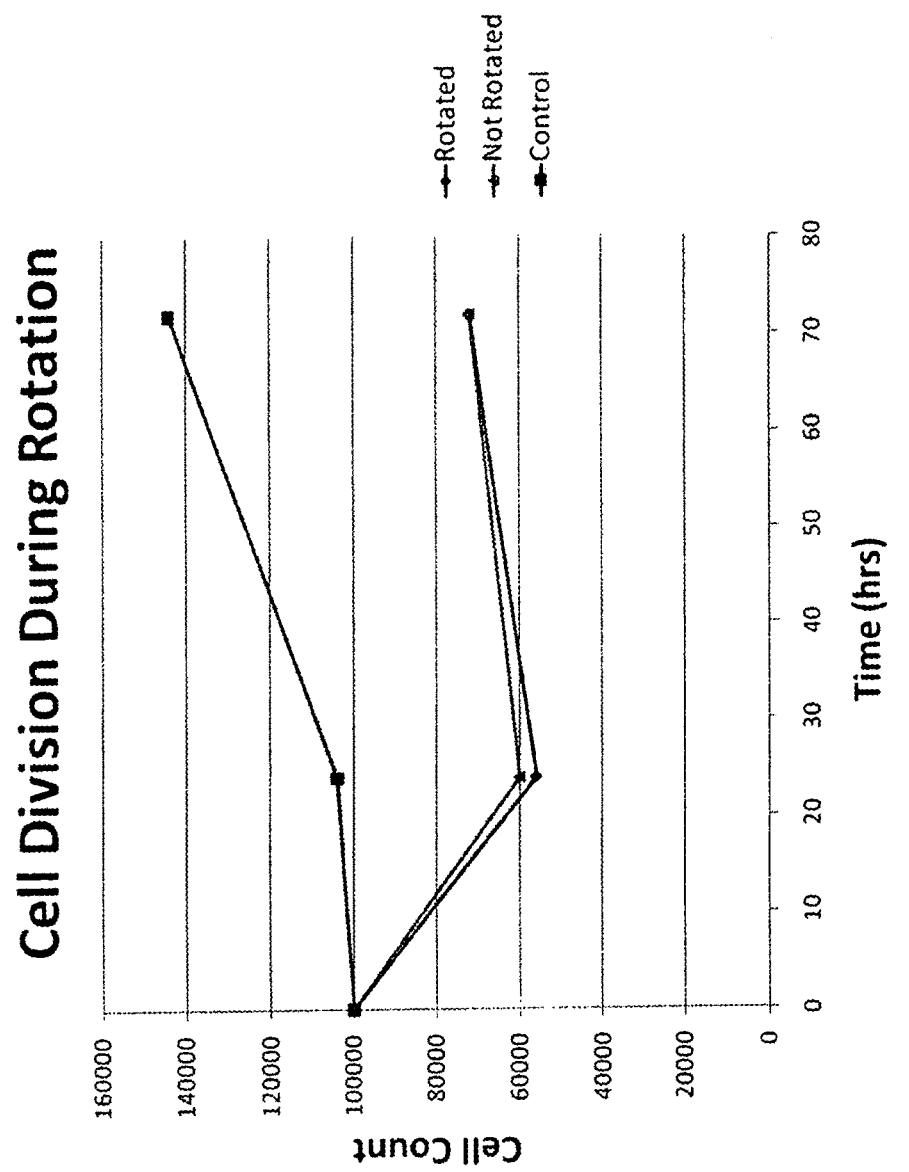
FIG. 10 illustrates the effect of rotation on cell division.

Finally, we also tested the effect of magneto-rotation on cellular division. The question was: does magneto-rotation impede immediate cell division? To investigate the short term impact, we rotated cells on agarose for 72 hours, and compared cell growth with two other controls (non labeled and magnetically labeled cells in the absence of magnetic field). We found no difference between the two different groups of magnetically labeled cells (see FIG. 10). This also rules out any potential magnetic hyperthermia happening during rotation.

The use of magnetic nanoparticles and alternating magnetic fields has been commonly associated with hyperthermia, a process where the vibrating nanoparticles inside the cells produce heat, eventually killing the labeled cells through a rise in temperature. As a consequence, the ability to rotate cells through the internalization of similar magnetic nanoparticles and the application of a rotating magnetic field, i.e., alternating in two directions at the same time, without causing harm to the cell has been a concern, even though we are using much lower fields by an order of magnitude, and frequencies in the ranges of a few dozen Hz instead of a few 100 kHz.

Our first concern was then to assure that the rotation in itself did not kill the cells. Our results show that the viability of the cells is preserved while they are rotated. Also the exposure to a (weak) laser (in order to capture a scattering signal from the rotating cell) does not have any effect on short term cell viability, as shown in FIG. 3B. However, the presence of a laser is not necessary; and the signal can also be analyzed through a camera, removing any long time risk that a long term exposure to a laser beam could cause.

Our results also show that the internalization of magnetic nanoparticles does not cause any effect on cell viability, and it only affects cell division by reducing the growth rate for a short time, over a limited number—at most 3—of cell cycles, before reaching normal rates. Indeed, our magnetically labeled cells have been successfully subcultured in petri dishes; and we observed no difference in viability (see FIGS. 9 and 10) or in proliferation rates after three division cycles (data not shown). In accordance with previously published data, we also found that magnetically labeled cells grew at a slower rate than non-labeled cells, up until three division cycles, from which point onwards the growth rates were back to normal (see FIG. 10). Also, as mentioned, according to Arbab et al. the presence of cell internalized magnetic nanoparticles does not cause deleterious long term effects on the viability of the cells (over a period of 5 to 7 division cycles, i.e. over several weeks).

The presence of a rotating magnetic field, and the induced sub-hertz frequency rotations that were induced in the magnetically labeled cells did not have along term impact on cell division, as shown by our clonogenic assay and by the cell count, after rotating cells for 24 to 72 hours.

Therefore, we have shown that for magnetorotation any cell death observed was the consequence of a purposely-induced toxic environment. In addition, we anticipate that since cells do not die as a result of rotation, cell growth, and even critical dormancy studies could be performed. It is worth noting that cell division has been observed during rotation, and rotating cells do not seem to have a different division rate compared to magnetically labeled non-rotating cells. All in all, the difference in growth rate observed during rotation can be definitely associated with the labeling of the cells with nanoparticles, and not the impact of rotation itself.

Thus the present techniques can provide advantages in terms cell viability compared, for instance, to cell electrorotation methods, which use the cytoplasm non-uniformity to induce an electric dipole and can cause the rupture of the plasma membrane, resulting in cell death, at lower frequencies. Cell magneto-rotation preserves the viability of the cell, both on a short and long term perspective (e.g., 3 weeks). The rotation in itself does not affect cell growth.

As described, the present techniques demonstrate an ability to monitor cell death using the change in rotation rate of a magnetically labeled cell. The morphology of the cell has been successfully linked to cell fate, since we could associate the formation of blebs during cell death with a significant slowdown in rotation rate. With the present techniques, we were also able to characterize cell death with a typical rotation trend, namely the exponential-shaped curve of the rotation period over time. Compared to a live/dead cell assay, we can detect cell slowdown as early as with fluorescence methods, if not earlier. Indeed, blebs are formed while the cell is dying, at a point where the cell membrane is still impermeable to the fluorescent dyes (here, propidium iodide). These results not only show the ability to discriminate cell death from the rotation curve shape, but also the compatibility of the method with a fluorescence assay. To this end, cell magneto-rotation can also be used as a way to maintain single cells in a non-adherent and localized fashion.

Another advantage of the presented method is its ability to track the very same cells over extended period of times. Indeed, fluorescent dyes are subject to photobleaching, affecting the evanescence of the intensity of the light emitted by the dyes. In order to monitor a phenomenon over time, it is then necessary to use different groups of cells that will be stained at different points of time.

As much as cell-to-cell variation can be screened by variations in fluorescence intensity in a cell sample, variations in the trends of cells' rotational periods can also give insights into cell-to-cell variability/heterogeneity. For instance, we can track this heterogeneity not only through the amount of iron-nanoparticles loading into the cell, but also through the time it takes for the rotational period to double under toxic conditions, in a similar fashion to the way the radiation half-life is measured for radio-active atoms. This way, the average "doubling time" will give a frame of reference for the entire cell population, while its distribution among cells in the same population will be a source of information regarding its heterogeneity.

These above-discussed techniques may be implemented on single cells, either separately or at a small throughput (between five to ten at the same time), and, in other examples, may be implemented on more robust and perfected multiplexed arrays, with at least a few hundred cells, which would be the relevant quantity regarding circulating tumor cells. Cell magneto-rotation, rather than competing with techniques such as flow cytometry, complements them by extending the reach of the assays to rare cell populations that are naturally found in suspension, and by preserving them in this state while performing the assay.

In any event, the magneto-rotation techniques may be used to monitor morphology changes of circulating tumor cells (CTCs) in suspension, at the single cell level. These cells are both very rare and, as stated by their name, are in suspension. They can even circulate in the bloodstream for months or longer without attaching to any surface. This phenomenon, coupled with dormancy and repopulating potential, explains why patients who seemed apparently cured had developed one or several new tumors. In terms of adaptability, of course, these techniques can equally be used in serum.

In some examples, techniques are able to monitor morphology changes occurring in single cells in suspension. The magnitude of the shear stress acting on the cell while rotating, is of the same order of magnitude as that in the bloodstream (20 to 40 dynes/cm$^2$). It has to be noted though that shear stress in the bloodstream is not uniformly distributed in space and in time (due to heart pulses). Instead of a moving environment, the cell itself performs a relative motion, the advantage being that the cell stays highly localized, without the need to be attached or constrained, which would be the case if we wanted to track single cells in a flowing stream. In addition, it has been shown that gene expression and cell signaling are significantly different for cells grown on a 2D pétri dish compared to those grown in 3D. Once plated, clinical samples might also express a different phenotype than their suspended counterparts, a phenomenon that could be studied using Cell Magneto-Rotation. In the meantime, traditional assays, such as flow cytometry and MTT assays, have been relying on mass numbers and plated cells.

Hence, we see their potential inadequacy when it comes to toxicity assays of CTCs: the impossibility to perform these assays on a reduced number of cells (a few dozens), and, more seriously, the risk of being irrelevant because of the difference in gene expressions, if not mutations, that occur if these circulating cells are plated. Applied to the rare CTCs, where every single cell could be a repopulating one, single cell identification and assessment is valuable. Another important feature that these cells exhibit is dormancy. They can stop growing for prolonged periods of time. Furthermore, as much as it is vital to eradicate all intratumoral subclones, as stated by Notta et al., the most useful anti-cancer therapies will also have to eradicate all the subclones in the circulating cell population so as to prevent metastasis. Such drug sensitivity tests may be performed using the CM method, as a complementary technique to the present. In addition, the magneto-rotation test can be used coupled with a camera instead of a laser beam (or an LED), and thus does not necessitate a complex optical setup besides the microscope. Because a dormant cell is alive but does not grow, its rotation rate should not vary under non-toxic conditions, even after a period of time corresponding to a full cell cycle. Thus our approach could allow us to discriminate dormant cells from the general population.

HeLa cells were used in the present techniques, because of their ability not only to survive but also to grow in suspension. We observed the formation of filopodia in healthy cells during rotation. Filopodia are spikes that are responsible for cell motility, migration and fixation to a substrate. However, because filopodia are oriented toward the outside of the cell, these morphology changes were sufficient to affect the rotation rate. It is not clear yet whether filopodia formation is a result of rotation or a process that would occur anyways to cells in suspension. However, filopodia, or other protrusions, might not be formed in cells while circulating, but it is very likely that they appear when these circulating cells try to attach to the endothelium in order to reach for tissues and/or secondary tumors. As such, magneto-rotation on protrusions is another useful application to research effort on cell adhesion.

Thus the present techniques describe a single live cell analysis system that can monitor cell morphology through the related effective volume changes, in suspension, without affecting cell viability. Specifically, we have demonstrated the ability to use cells as rotating magnetic microplatforms, through the uptake of functionalized magnetic nanoparticles, and the ability to control and measure their rotation under near real-time conditions. Cell death, and the dying process can simply be monitored through changes in the cell's rotational period. This lends itself to rapid drug sensitivity testing on cancer cells, with no need for cell culturing. The techniques may be used as fortests on the rare and fleeting (due to differentiation) cancer stem cells. While circulating, the dormancy of these cells could also be evaluated this way, via the observed stability of their rotation rate. The methodology used here is very general, and can be used with various cell types (tumor, stem cells, red blood cells), and in various media. Also, this micro-system can be operated on a range of supports (cell imaging plate, agarose layer, inverted droplet, PDMS micro-channel), and the magneto-rotation method can also be applied to the rotation of other systems, such as cell clusters or spheroids. The CM method herein described is adaptable to various biotechnology applications, e.g., drug discovery or testing, and to growth assays, all performed in a three dimensional environment. Furthermore, CM integration allows for integration into an in vivo magnetic enrichment process, followed by ex vivo monitoring, for tailor-made therapies.

In an example, the magnetic particles (nanoparticles) were functionalized by coating with poly-L-lysine. For example, to magnetically label HeLa cells, 30 nm amine coated magnetic nanoparticles (OCEAN NANOTECH) were functionalized using poly-L-lysine (PLL, Sigma Aldrich GmBH), a transfection agent that improves the internalization in cells. A solution of 200 ug/ml of nanoparticles in DMEM was mixed with 10 uL of PLL, and rotated end-over-end in a vial at room temperature for 1 hour. The particles solution was then filtered using a 0.2 um filter (WHATMAN Nylon Filter Media) to remove any biological agents that could contaminate the sample. The filtered solution was immediately used.

Cell culture and labeling of the HeLa 229 cells (American Type Culture Collection) was performed by culturing the HeLa cells for four days in growth media of DMEM (INVITROGEN), 10% FBS, 1% PSG and 25 ug/ml (prior to filtration) of functionalized magnetic nanoparticles (OCEAN NANOTECH). The growth medium was removed, and cells were washed once, using PBS, before adding Cell Detachment Buffer (GIBCO). This enzyme free buffer does not affect surface proteins during cell removal from the dish, and allows the nanoparticles which could have attached the surface of the cell to be retained. After 30 min of incubation in the detachment buffer, cells were washed with DMEM, and centrifugated (for the preparation of fixated cells, this step was replaced by magnetic separation in order to keep the cells from forming clusters). Cells were resuspended in fresh media.

Before rotation, 300 uL of the cell solution was introduced into a LIVE CELL ARRAY plate (NUNC), with 100 um wells. Cells were then pulled to the bottom of the plate using a permanent magnet. Once cells were pulled down to the wells, the plate was placed inside the coils, with the wells in the center.

Fluorescent imaging was made using 3 ml of magnetic nanoparticles (tagged with poly-L-lysine) at a concentration of 200 ug/ml in DMEM were mixed with 3 mg of HPTS fluorescent dyes. The mixture was vortexed and then put under end over end rotation for one hour before being centrifuged at 9000 rpm for ten minutes in Amicon® Ultra centrigugal filters Ultracel® 3k. The particles tagged with the fluorescent dyes were then resuspended in DMEM at the initial concentration of 200 ug/ml.

Custom Helmholtz coils were integrated on the platform of an OLYMPUS BX50WI microscope. Each pair of coils produced a field parallel to the imaging plane and was plugged into an amplifier (amplification factor during rotation was set to 1), which, in turn, was plugged to two function generators with a 90 degree phase shift (Agilent Technologies Arbitrary Waveform Generator 33220A, 20 MHz function). Both power supplies were set to provide a sine wave function, with amplitude of 3V. The phase shift was controlled with an oscilloscope (Agilent Technologies, DSO5012A). Finally, the magnitude of the magnetic field was measured using a magnetic probe placed in the center of the magnetic coils (3 Axis Magnetic Field Transducer, C-H3A-2m_E3D-2.5 kHz-1%-2T, Sensitivity 5[V/T], SENIS GmbH).

Figure 4:
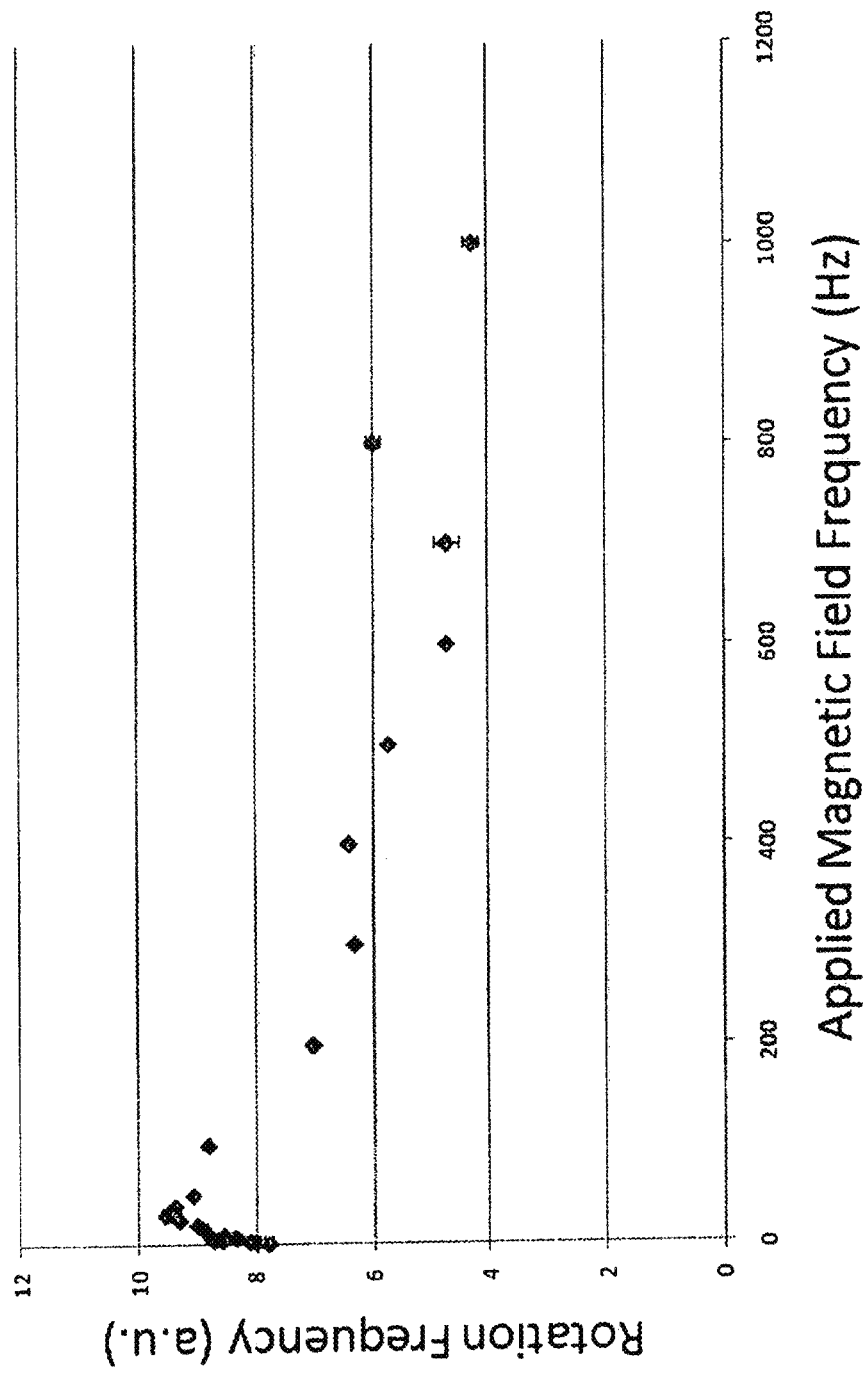
FIG. 4 shows the frequency response of a fixated cell (error bars are inside the dots, values represent mean+/−0.5*s.d., n=18).

FIG. 4 shows the frequency response of a fixed cell.

The laser in the example was an unstabilized HeNe laser (SPECTRA-PHYSICS 136/P), with a wavelength of 632 nm. Data were acquired using a Labjack UE9 data acquisition device, receiving the diffraction signals from a non amplified photosensor. The data were recorded analyzed on a computer (DELL, INTEL CORE2 Duo CPU E6550 at 2.33 Ghz, 1.98 GB RAM, Microsoft WINDOWS XP Professional Version 2002 SP3) using customized software (LabView).

The longest cell rotation period used was on the order of one minute, which is the case when the cell's blebbing created a large cell and a high effective volume. At the beginning of the experiments, the rotation period was usually comprised between 1 s and 15 s. To analyze the signal, we measured and average the rotation period over a moving time window of at least 10 periods. In the early stages, we needed a 30 s time window, and when the rotation rate becomes very low (30 s), we used a time window of around 3 min (even though at this point, a statistical averaging of the rotation period is not relevant since the length of the period reduces the error made on the measure).

Image acquisition was made through a Digital Camera (Mightex Monochrome Camera MCE-B013-US, 1.3 Mega-Pixels), and images were recorded with the Mightex acquisition software (v1.1.0, 1280×1024, Exposure Time 35 ms). Image capture was realized via an external trigger, programmed on LabView.

The laser power was measured using a power-meter (Coherent Calibration Tag, MIL-STD-45662-A). Before reaching the microscope's mirror (namely after its transmission through the condenser), the power measured was of 1.45 mW. On the microscope platform, the power was between 125 uW+/−2 uW.

To first explore the incubated cells' magnetic behavior, cells were fixated with a solution of 3.7% formaldehyde in phosphate buffered saline. This way, the cross-linking of the proteins, both in the membrane and in the cytoplasm, removed any potential effects of changes to the drag, resulting from morphology changes. A single cell was thus tested under different field frequencies, keeping the other conditions constant. The cell mimicked the magnetic response behavior of a superparamagnetic micro-bead that was manufactured in an analogous way, e.g. iron-oxide nanoparticles (magnetite) loaded into a polystyrene bead, such as the DYNABEADS. The magnetic response is shown in FIG. 4. At frequencies ranging from 1 Hz to 1 kHz, cells rotate in an asynchronous manner. Indeed, while the field rotates at frequencies above 1 Hz, cells rotate at much lower frequencies. Being in the asynchronous regime is crucial to the described magneto-rotation method. When in this regime, any small change in the cell shape (or in the liquid medium's viscosity) immediately translates into a change in rotational period. Otherwise, in the synchronous regime, the cell would keep the same rotation rate, i.e. would faithfully follow the driving magnetic field, with an identical rotation frequency, irrespective of cell or medium changes. As previously reported, we note the presence of a maximum rotational frequency beyond which the rotation frequency of the cell decreases with an increase in the applied driving frequency.

Given that the cell is already in the asynchrous regime at frequencies of 1-1,000 Hz, we can set the applied field frequency so that the cell rotation frequency is at its highest (which occurs for driving frequency at 100 Hz), compared to when at other applied frequencies. This way, the effects of surface friction on rotation are reduced to a minimum and the sensitivity to drag and shape increases, as well as the real time resolution.

Theoretical Analysis of the Equation of Motion of the Cell

The magnetic torque of the magnetized cells is given by the following expression:

$$\vec{\tau}_{mag} = \vec{m} + \vec{B} = (\vec{m}_{perm} + \vec{m}_{ind}) \times \vec{B}$$

where $\vec{\tau}_{mag}$ is the total magnetic torque of the cell, $\vec{B}$ is the external magnetic field and $\vec{m}$ is the magnetic moment of the cell. The latter is the sum of the permanent magnetic moment $\vec{m}_{perm}$ and the induced magnetic moment $\vec{m}_{ind}$.

With $\Omega$ the frequency of the applied magnetic field and $\chi(\Omega)$ the magnetic susceptibility of the cell, we get:

$$\vec{\tau}_{mag} = \vec{m}_{perm} \times \vec{B} + \text{Re}\left[\chi(\Omega) V_m \frac{\vec{B}}{\mu_0}\right]$$

-continued $$= \left[m_{perm}B\sin(\Omega t - \theta) + \chi''(\Omega)\frac{B^2}{\mu_0}V_m\right]\vec{e}_z$$

where $V_m$ is the volume of the magnetic content of the cell, $m_{perm}$ the norm of the magnetic moment, B is the intensity of the applied magnetic field, $\mu_0$ is the permeability of the free space, and $\chi''(\Omega)$ is the imaginary part of the magnetic susceptibility of the cell. The non-zero imaginary part of the magnetic susceptibility of the superparamagnetic nanoparticles is the element responsible of the presence of a non-zero induced torque along the z-axis.

As can be seen, the magnetic torque is an additive sum of two contributions: a permanent one, and an induced magnetic moment.

However, in DMEM at room temperature, the critical frequency of the cell has not been observed (FIG. 4), and, as a consequence, for $\Omega$=100 Hz, the permanent magnetic torque is negligible. We are thus left with:

$$\vec{\tau}_{mag} = \chi''(\Omega)V_m\frac{B^2}{\mu_0}\vec{e}_z$$

Finally, applying Newton's second law of motion to the rotating cell, neglecting the cell's moment of inertia and the Brownian forces, one finds the following equality of the driving magnetic torque and the opposing torque derived from viscous forces:

$$\tau_{mag} = \tau_{drag} = \kappa\eta V\dot\theta$$

With $\kappa$ the shape factor of the cell, $\eta$ the viscosity of the medium, and V the total volume of the cell. The angular speed is then found to be given by:

$$\dot\theta = \frac{\chi''(\Omega)V_m B^2}{\kappa\eta V\mu_0}$$

Since the magnetic content of the cell does not significantly change over the course of the measurement, we can assume that $V_m$ and $\chi''(\Omega)$ are constant. As a consequence, the rotational speed is inversely proportional to the product of the shape factor by the volume, namely the effective volume of the cell:

$$\dot\theta \alpha \frac{1}{\kappa V} = \frac{1}{V_{\it{eff}}}$$

We thus deduce for the rotation period:

$$T = \frac{2\pi}{\dot\theta}\alpha V_{\it{eff}}$$

Magneto-Rotation sensitivity compared to optical sensitivity was assessed in this example, by assessing the accuracy of the method regarding effective volume modifications. We compared the trends in the effective volume (proportional to the rotation period) with those of the surface area as estimated from microscopy images (which is a standard indicator of the cell morphology/shape factor). With an imaging software (ADOBE PHOTOSHOP), we estimated the surface areas of the cells at regularly spaced intervals. As we can see on FIG. 5, magneto-rotation is as effective as an optical setup for small changes. However, for bigger changes, magneto-rotation amplifies the response compared to the optical setup. Significant loss of magnetic content takes several days. Thus its impact on the interpretation of the results, after several hours, can be ignored. Also, the steady rotation rate of a control cell tends to confirm that the loss of magnetic content is not significant over the time-span of the measurement. Otherwise, the magnetic moment of the cell would critically decrease, and the cell would slow down significantly, which is not the case (FIG. 3b). Therefore, we can rightfully assume that the effective volume is indeed proportional to the rotational period.

Viability after Laser Exposure was demonstrated and is illustrated in FIG. 3B. Cells were incubated with nanoparticles following the protocol described above for 48 h. Cell count gave a cell density of 156000 cells per ml. Trypan blue viability tests were then realized at different time points to evaluate the influence of laser exposure on cell viability. T=0 corresponds to the time cells were resuspended in fresh medium after being washed, detached from culture plate and centrifuged.

Three counts were done for T=0. To measure the viability after 120 min, 150 ul of undiluted cells were put into the wells of a 96-well plate. One of the two wells was exposed to the laser, the other one not. For each sample, four cell counts were realized. The error bars represent one standard deviation. The results show that there is no significant difference in terms of viability for cells after a laser exposure of two hours.

EXAMPLE 2

Study of Cell Aggregates

As mentioned above, cells may be aggregated or allowed to aggregate. The cells, which have internalized magnetic particles, may then be rotated and examined as an aggregate or cluster. The magnetic moments of the magnetic particles within each of the cells will sum, allowing rotation of the entire cluster in the presence of a rotating magnetic field. By examining the rate of rotation, changes in cell size, number, morphology, etc., particularly in response to outside conditions, may be monitored. Cell clusters or aggregates in suspension may be a particularly valuable model for understanding biological processes such as tumor formation and treatment.

In one example, HeLa cells in growth media were put in inverted droplets, hanging from the top slide of a petri dish. The bottom part of the petri dish was filled with 10 ml of PBS, in order to avoid evaporation. Depending on the density of cells present in the droplets, the micro-tumor formation may take between 24 h to a week (it does also depends on the cell line). After formation of a spheroid, magnetic nanoparticles were injected in the droplet, and the spheroids magnetized. This may be advantageous to using magnetized single cells to form the spheroids, as preliminary results show, in terms of growth rate, tumor integrity and amplitude of the magnetic moment. Sensitivity may be improved in this way.

The spheroids can then be taken out and rotated in different environments (e.g., in inverted droplets, standard well plates, surface treated slides, microfluidic device, etc.). Preliminary results show that rotation rate and morphology changes are related the same way as for single cells, allowing studies on tumor formation, growth and evolution of a micro tumor when changing the environment conditions.

Figure 7B:
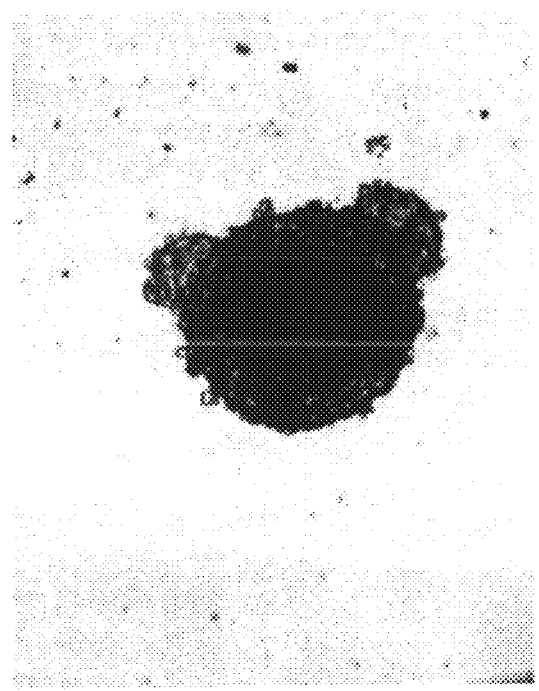
FIGS. 7A and 7B show HeLa cell spheroids.
Figure 7A:
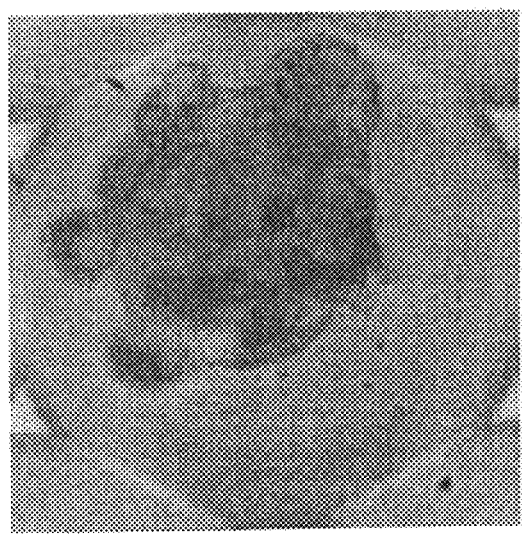
Figure 8B:
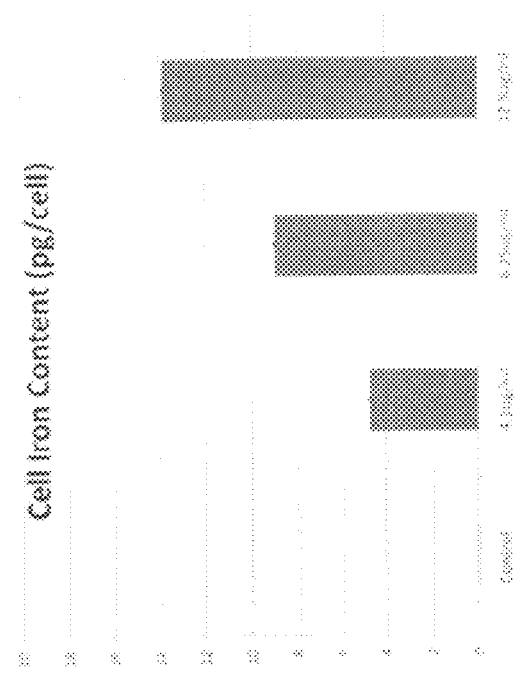
FIGS. 8A and 8B show the nanoparticles localization and concentration in cells after incubation.
Figure 8A:
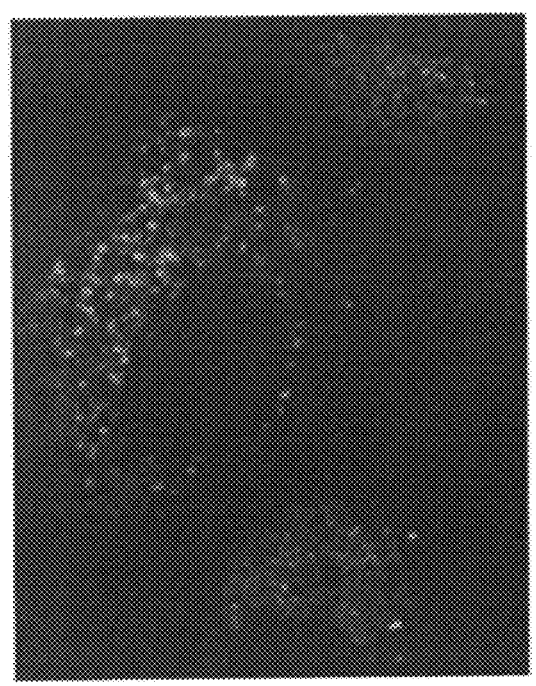

FIGS. 7A and 7B show HeLa cell spheroids. In FIG. 7A, the spheroid is about 100 µm wide, and are made of a few dozens of cells, while in FIG. 7B the spheroid is made of more than a thousand cells (it is also wide enough to be visible without a microscope, at least 500 um).

Different types of cells (normal, stem cells or malignant cells) could be associated to study three dimensional tissue formation, cell differentiation and cell-cell interactions in tissues. As mentioned, in general, the systems, devices and methods described herein may be used with any cell or type of cell.

Detection and/or Measurement of Internalization

The methods, systems and devices described herein may also be used generally to detect, measure, and/or estimate the rate or amount of internalization of magnetic particles into analytes, such as cells. For example, the systems described herein may be used to determine a rate of internalization of magnetic nanoparticles in one or more cell types under various conditions. Rates or levels of such nanoparticle internalization may be particularly useful in applications in which nanoparticles are used in vivo to treat cells such as cancer cells or the like, using drug coatings, heating, etc. For example, in some variations, magnetic (or non-magnetic) nanoparticles may be used to facilitate imaging (e.g., by enhancing MRI). The in vitro determination of rates of internalization in one or more cell types that may be determined under different parameters described herein may be used to extrapolate reasonable in vivo rates. The parameters of the internalization may be varied, including the use of different cell types, as well as spheroids, clusters or individual cells.

In other examples, the techniques described herein are directed to the detection of an analyte by binding the analyte to both a non-magnetic substrate and a magnetic label, so that the application of a rotating magnetic field (e.g., at a constant rotation rate) will cause rotation of the resulting complex (substrate/analyte/magnetic label) at a rate that is characteristic of the binding. For example, this technique may be used as part of an assay to determine concentration of an analyte.

A schematic representation of the sensor is shown in FIG. 11. In this example, the setup includes three components: 6.7 µm streptavidin-coated solid phase spheres (substrate), 40 nm biotin-coated particles serving as an analyte mimic, and 1 µm streptavidin-coated superparamagnetic label beads. FIG. 11 demonstrates the concept of label-acquired magnetorotation: the sandwich complex (substrate with bound analyte and bound magnetic label) rotates only when it has acquired magnetic labels, and rotates faster with additional analyte. The result is the label-acquired magneticrotation of the sandwich, providing an assay for the detection of a biological target.

EXAMPLE 1

In the setup in FIG. 11, the analyte is a bead that is coated with biotin. The biotin-coated particles serve as a mimic for an analyte. In operation, biotin and streptavidin may be replaced by analyte and analyte-binding molecules or complexes (e.g., proteins and antibodies).

Figure 11A:
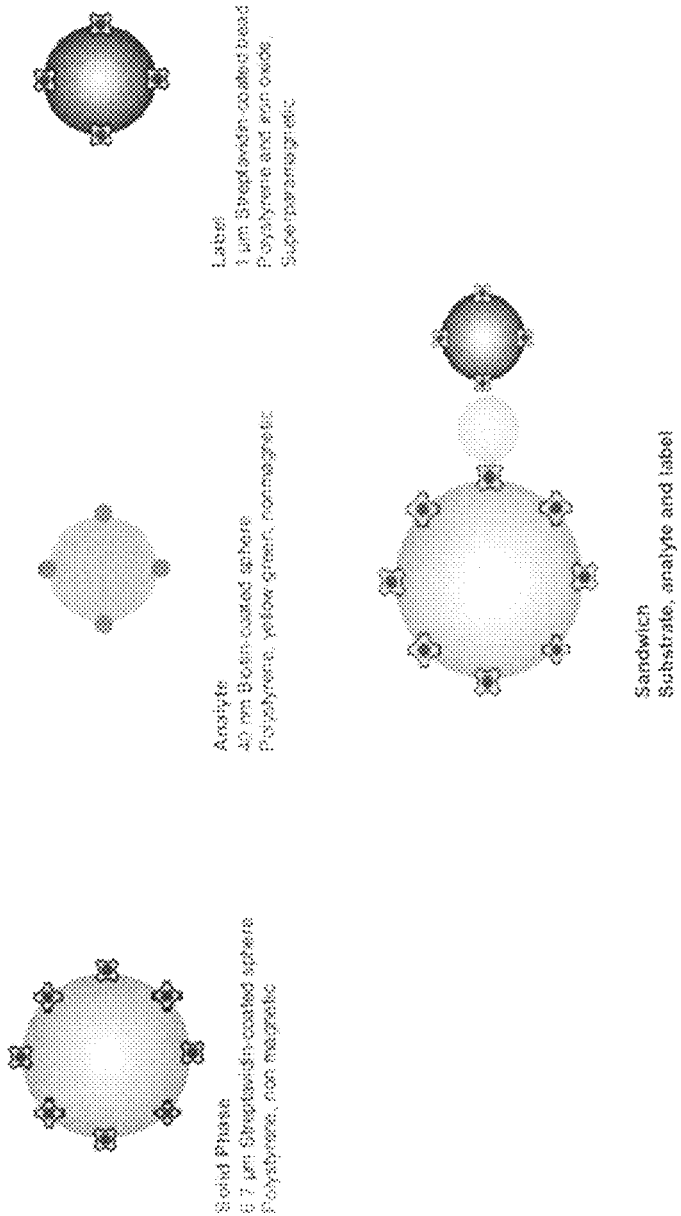

As indicated in FIG. 11a, solid-phase spheres served as the substrate (mother) spheres in this example. The solid-phase 6.7 µm Streptavidin-coated spheres were polystyrene, non magnetic spheres. The analyte in this example was 40 nm Biotin-coated sphere Polystyrene, yellow-green, non-magnetic spheres. The magnetic label was 1 µm Streptavidin-coated beads of polystyrene and iron oxide, which were superparamagnetic.

Figure 11D:
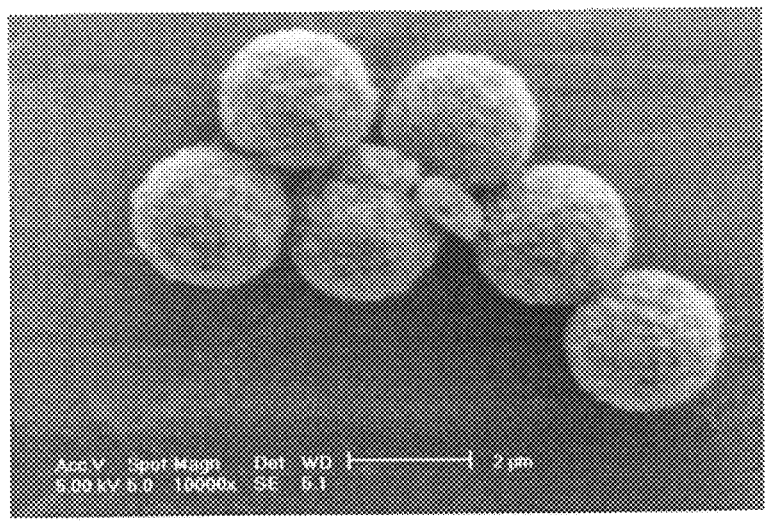
FIG. 11d shows one variation of superparamagnetic beads that may be used as a label.
Figure 11E:
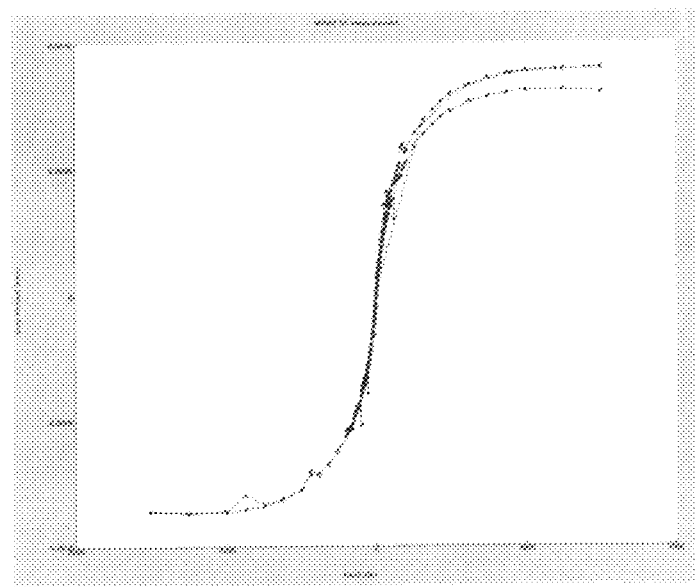
FIG. 11e shows a hysteresis curve for magnetization of the magnetic particles shown in FIG. 1d.

Any appropriate magnetic label may be used, particularly small labels (e.g., magnetic microspheres or nano-spheres); in some variation the magnetic labels are magnetic nano-spheres having a diameter less than 100 nm. FIG. 11d indicates one variation of superparamagnetic beads (having diameters on average of about 3 µm). The beads in this example are composed of polystyrene embedded with many superparamagnetic nanoparticles. These beads are characterized by hysteresis-free magnetization, as illustrated in FIG. 11e.

In this example, buffer was used to wash and suspend the substrate, antigen and magnetic markers. In practice, any appropriate suspension and/or washing solution may be used. For example, 1× Dulbecco's Phosphate-Buffered Saline (PBS) and Tween-20 (surfactant) were used. 10% Bovine Serum Albumin (BSA) Blocker solution was also used to wash. For example, 6.7 µm streptavidin-coated polystyrene solid phase spheres (Spherotech, Lake Forest, Ill.), with density $\rho=1$ g/cm$^3$, were washed three times by centrifuging and discarding the supernatant. The spheres were then resuspended and diluted 1:10 in a PBS solution that contained 0.1% Tween-20 and 0.1% BSA (which will be referred to as PBS-TB) to reduce nonspecific adsorption, resulting in a final concentration of $3.02\times10^3$ spheres/µL. 40 nm yellow-green fluorescent biotin-coated particles (Invitrogen, Carlsbad, Calif.) were diluted in PBS-TB to final concentrations ranging $1.62\times10^5$-$5.12\times10^7$ particles/µL. 10 µL of the diluted 6.7 µm streptavidin-coated solid phase spheres were mixed with 10 µL of each biotin-coated particle solution and incubated end-over-end on a Sarmix SR1 (Sarstedt, Numbrecht, Germany) rotating mixer for 18 h. Excess biotin-coated particles were removed by centrifuging the solution and discarding the supernatant three times, and the sample was then resuspended in PBS-TB. This step prevented the streptavidin-coated superparamagnetic label beads from clumping. Successful binding and washing were confirmed by fluorescent microscopy with a 488 nm wavelength light excitation.

One (1) µm Dynal T1 streptavidin-coated superparamagnetic label beads (Invitrogen), $\rho=1.8$ g/cm$^3$, were washed three times, and were then resuspended and diluted 50× in PBS-TB, for a final concentration of $1.94\times10^5$ beads/µL. Two microliters of the biotin-coated 6.7 µm spheres and 2 µL of the 1 µm streptavidin-coated superparamagnetic label beads were mixed and diluted with 26 µL of PBS-TB, and then transferred to a well on a non-binding surface 384-well plate (Corning, Corning, N.Y.). The components were incubated at room temperature for 4 h. During the incubation, the 1 µm streptavidin-coated superparamagnetic label beads bound to the exposed biotin-coated particles on the 6.7 µm streptavidin-coated solid phase spheres, forming sphere-particle-bead sandwich complexes. A coverslip fluidic cell was fashioned between two 22×40 mm No. 0 thickness coverslips (Pierce, Rockford, Ill.) separated by a single piece of double-sided clear tape (3M, St. Paul, Minn.). The sandwich complexes were transferred from the 384-well plate and pipetted into the coverslip fluidic cell. The ends of the fluidic cell were sealed with Apiezon L grease (Apiezon, Manchester, UK) to prevent convection, drift and evaporation.

Figure 12:
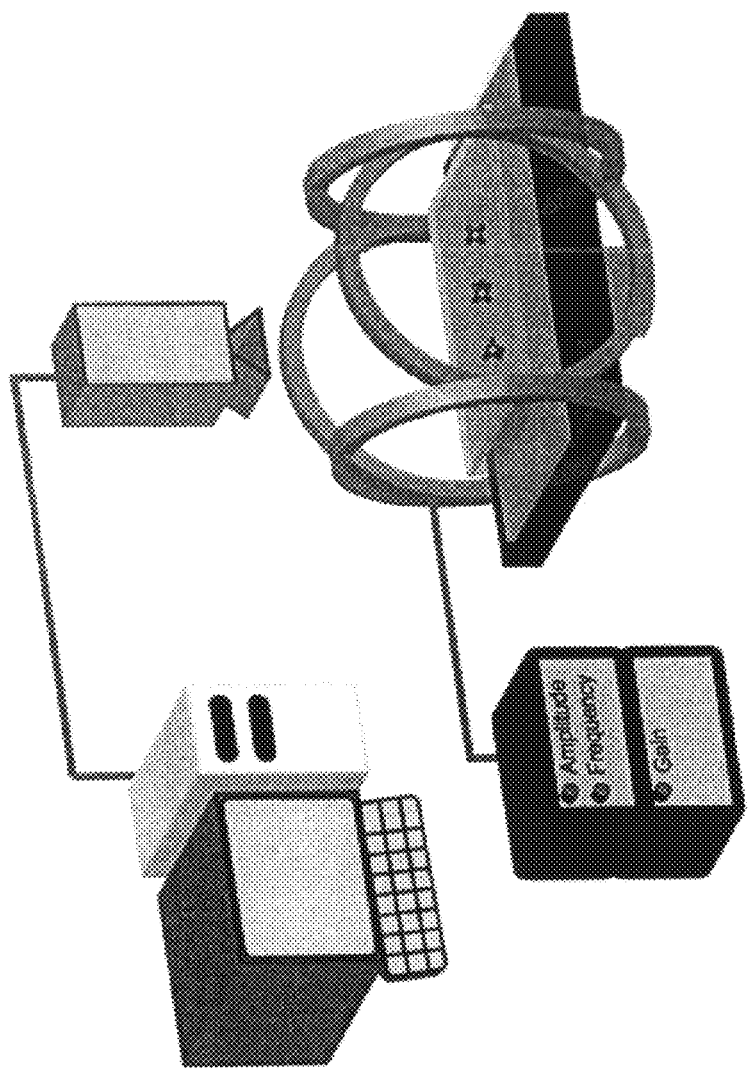
FIG. 12 is a schematic representation of the setup used in some variations. In this example, sandwich complexes are pipetted into a coverslip fluidic cell. A rotating magnetic field is created by two orthogonally oriented Helmholtz coils with each coil wrapped with 90 turns of copper wire. The field is controlled by a function generator and an amplifier. Parallel coils are considered part of a "pair". The pairs are driven 90° out-of-phase with each other. The spheres are observed through 60× and 100× optical microscope objectives connected to a digital camera. Videos may be analyzed to determine rotational frequency.

A schematic representation of the experimental setup is shown in FIG. 12. In this example, the system includes a stage (e.g., microscope stage 100) for holding the sample, and a camera 102 for detecting rotation of the sandwich, and controlled by a computer with input and display, such as an imaging processing system or portion thereof or other control system. An applicator 104 for applying a rotating magnetic field is integrated with the stage/holder. In this example, the applicator 104 includes a plurality of coils (e.g., orthogonal Helmholtz coils 106), although any appropriate setup for applying a rotating magnetic field to the sample may be used. The applicator coils are connected to a function generator 108, also part of the applicator 104, for controlling the energy applied to drive the rotating magnetic field at a constant rate (e.g., between about 10 Hz and about 1 kHz; in this example the rotation rate was 20 Hz).

As illustrated in FIG. 12, the rotating magnetic field was created with a pair of orthogonal Helmholtz coils that fits onto an inverted microscope. One pair of coils was driven by a sine wave, and the other pair was driven by a cosine wave, generating a uniform rotating magnetic field between the coils. The driving frequency and amplitude were controlled by an in-house custom-built function generator and amplifier. The field in the center of the coils was 1 mT rotating at a frequency of 20 Hz, as measured by a 3-axis magnetic field transducer (SENIS GmbH, Zurich, Switzerland). The rotation of the spheres was observed using two setups. The first was an Olympus IMT-2 inverted microscope (Olympus, Melville, N.Y.) connected to a Photometrics Cool Snap ES camera (Roper Scientific, Trenton, N.J.). Videos were recorded on a computer using MetaMorph (Meta Imaging Software, Downington, Pa.). The second was an Olympus IX71 inverted microscope with an oil-immersion 100× objective connected to a Basler piA640-210 gm camera (Basler, Highland, Ill.). Videos were recorded on a computer using an in-house program written in LabVIEW (National Instruments, Austin, Tex.). Videos were analyzed using the St. Andrews particle tracker (with custom modification to allow for tracking of angular orientation), a sophisticated LabVIEW-based particle tracking program.

In other variations, any sensor/detector for detecting the rotation of the sandwich complex (complexes) may be used; for example, the system may use frequency detection to determine the rotation rate. Although the example shown in FIG. 12 includes numerous multi-purpose elements (e.g., computer, microscope, microscope stage, coils, etc.) in some variations a dedicated system may be used that is capable and configured to detect rotation of one or more sandwich complexes.

In theory, the systems and methods described herein may be used to determine the concentration of analyte based on the concentration of magnetic particles bound. For example, the concentration of magnetic particles may be directly and linearly related to the concentration of analyte.

The system may operate by rotating the sandwich complex within an asynchronous magnetic rotation regime, in which the sandwich is rotated by the combined magnetic moments of the magnetic label particles bound to the sandwich (via the analyte) when driven by a continuously rotating magnetic field. In a (continuously/constant) rotating magnetic field, the magnetic moment of an object lags behind the field, resulting in a rotational frequency of the object (the sandwich) that is less than the rate of rotation of the magnetic field (e.g., rotational frequency of the field). This typically occurs above a critical frequency. Thus, the rotational frequency of the object (e.g., the sandwich or cluster of sandwiches) is a function of the size, shape, magnetic volume, and relaxation time of the object when above the critical frequency. This facilitates making quantitative measurements.

For example, for a magnetic object actively rotating in a fluid, the magnetic torque ($\tau_{mag} = m \times \mu_0 H$) and the rotational fluidic drag $$\left(\tau_{drag} = \gamma \frac{d\theta}{dt}\right)$$

oppose each other, and are the primary factors determining the rotational dynamics in a low Reynolds number environment. The magnetic torque is composed of the induced (e.g. paramagnetic and superparamagnetic) and permanent (e.g. ferromagnetic) magnetic moments of the bead. This relationship is expressed below:

$$\vec{\tau}_{drag} = -\vec{\tau}_{mag}$$

$$\vec{\tau}_{mag} = \vec{\tau}_{ind} + \vec{\tau}_{perm}$$

$$\gamma \frac{d\theta}{dt} = |(m_{ind} + m_{perm}) \times \mu_0 H|$$

where $m_{ind}$ is the induced magnetic moment of the bead, $m_{perm}$ is the permanent magnetic moment of the bead, $\mu_0$ is the permeability of free space, H is the magnetizing field, $\gamma$ is the drag coefficient, $\theta$ is the angular orientation of the object, and $d\theta/dt$ is the rotational rate in radians/s. Note that for this case, other forces, such as inertial and Brownian, are neglected. For a rotating body in fluid, $\gamma = \kappa \eta V_H$, where $\kappa$ is the shape factor (equal to 6 for a sphere), $\eta$ is the dynamic viscosity, and $V_H$ is the hydrodynamic volume of the rotating body. The magnetic torque arising from the induced magnetic moment can be obtained by combining the relationships $m_{ind} = MV_m$ and $M = \chi H$, where M is the magnetization of the material, $\chi$ is the magnetic susceptibility and $V_m$ is the magnetic volume. In a rotating magnetic field, the magnetic susceptibility can be separated into real and imaginary parts $\chi = \chi' - i\chi''$, corresponding to in-phase and out-of-phase components of the magnetization. When the above relationships are substituted into $\tau_{ind} = m_{ind} \times \mu_0 H$ and the cross product is carried out (namely $|(\chi'H - i\chi''H) \times H| = \chi''H^2$), one arrives the Equation below, which describes the torque arising from an induced magnetic moment:

$$|\tau_{ind}| = \mu_0 V_m \chi'' H^2$$

The torque arising from the permanent magnetic moment in a rotating magnetic field can be expressed as:

$$|\tau_{perm}| = |m_{perm} \times \mu_0 H| = m\mu_0 H \sin(\Omega t - \theta)$$

where t is time and $\Omega$ is the rotational frequency of the field. Combining these equations yields:

$$\gamma \frac{d\theta}{dt} = \mu_0 V_m \chi'' H^2 + m\mu_0 H \sin(\Omega t - \theta)$$

This equation describes the behavior of the rotating sandwich complex, composed of 1 μm superparamagnetic beads (with a small ferromagnetic component), in a rotating magnetic field. As mentioned, the magnetic beads used in this example are composed of 1 μm polymer spheres embedded with superparamagnetic nanoparticles. In the presence of a magnetic field, the magnetic moments of these nanoparticles align with the field, and can undergo Neel relaxation. If the frequency of a rotating field is sufficiently high, the magnetic behavior is dominated by the imaginary susceptibility, which has been discussed in detail in the literature. When dealing with only an induced moment, the above equation reduces to:

$$\gamma \frac{d\theta}{dt} = \mu_0 \chi'' H^2 V_m$$

When dealing with only permanent magnetic dipoles, this equation reduces to:

$$\gamma \frac{d\theta}{dt} = m\mu_0 H \sin(\Omega t - \theta)$$

This equation can be analytically solved.

For the frequency and magnetic field amplitude used in this example (e.g., 20 Hz and 1 mT) the rotation rate scales with the square of the magnetic field amplitude, as given by $d\theta/dt$ is proportional to $H^2$. Additionally, the rotation rate increases with increasing driving frequencies between 10 and 1000 Hz, which suggests dependency on imaginary susceptibility in the equations above. Both observations indicate that, under these conditions, the induced moment of the beads dominates over their permanent moment and is the primary cause of the driven rotation. As a result, we obtain the following relationship since other variables are constant during the experiments, and changes in the drag coefficient are assumed to be negligible:

$$\frac{d\theta}{dt} \propto V_m$$

For a collection of particles with induced dipoles, the total moment is approximated as the sum of the individual induced moments of each particle. Therefore, this relationship can be rewritten as:

$$\frac{d\theta}{dt} \propto N_{particles}$$

This dependence can be seen in FIG. 5b, and holds for materials that do not have permanent dipoles. Thus, the rotational frequency of a sandwich complex in a rotating magnetic field is a function of the number of 1 μm superparamagnetic beads in the rotating sandwich complex (expressed later in Hz (e.g. (½π)*(dθ/dt)). Assuming the beads attach proportionally to the concentration of the analyte, we can rewrite the relationship as:

$$\frac{d\theta}{dt} \propto [analyte]$$

Figure 6:
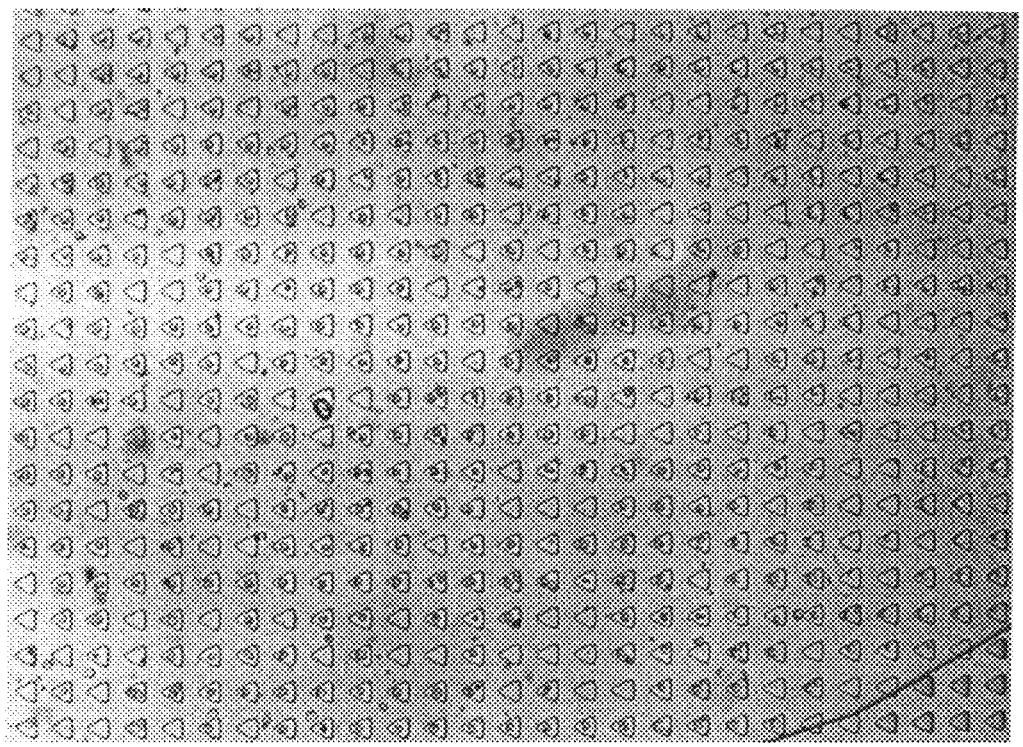
FIG. 6 illustrates multiplexed trapping of cancel cells using cell magneto-rotation, where the trapped cells are PC-3 cells (prostate cancer).

Indeed, this general behavior of an increased rotational rate with increased analyte coverage is observed over two orders of magnitude as shown in FIG. 6, and is discussed in detail below.

In this example, sandwich complex assays were performed with biotin-coated particles as the analyte, which mimic a biological target. The concentration of biotin-coated particles was measured by observing the rate of rotation of the (solid phase sphere)-(biotin-coated particle)-(superparamagnetic label bead) sandwich complex. The 6.7 μm solid phase sphere has a surface area of 141 μm². Given that a 40 nm biotin-coated particle would occupy an area of 1.26×10³ μm², one 6.7 μm sphere could bind up to 10⁵ biotin-coated particles. The superparamagnetic label beads have a diameter of 1 μm, and occupy an area of 0.866 μm², which, given the limits of the packing efficiency of spheres, suggest that 145 superparamagnetic label beads can bind to that surface. This configuration would be expected to produce a sensor with approximately 2 orders of magnitude of dynamic range, as indicated by the equations discussed above, assuming that the magnetic moments of the beads are additive. The position at which the beads bind to the sphere should mostly affect the rotation at low numbers of binding beads. A variation in the binding location of a few beads could affect the rotational speed, which would result from differences in location-dependent torque and drag. However, as the number of beads on the sphere increases, this effect will have a smaller contribution.

Furthermore, the 6.7 μm "mother" sphere is more than 300 times bigger than a 1 μm label bead, thus the binding of a single bead to the sphere should not significantly alter the sphere's center of rotation or shape factor. 1 μm beads were selected as labels for these experiments, so that they could still be individually distinguished by using light microscopy.

Figure 13C:
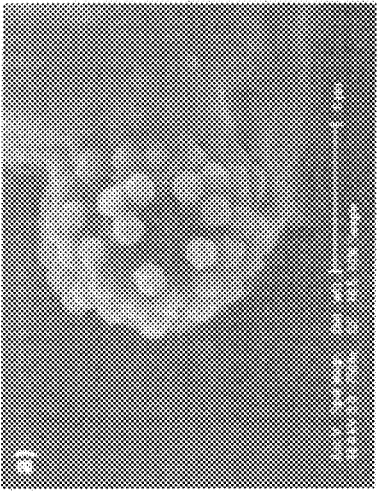
FIGS. 13a-c shows scanning electron micrographs of sandwich complexes (examples) incubated with three different concentrations of biotin-coated particles. For example, in FIG. 13a-c the concentrations of biotin-coated particles are $2.88\times10^7$, $2.88\times10^6$, and $2.88\times10^5$ $\mu L^{-1}$, respectively. The 1 μm superparamagnetic label beads can be seen attached to the surface of the 6.7 μm solid phase spheres. The structures in the background of these images likely resulted from salts left by the buffer after evaporation.
Figure 13B:
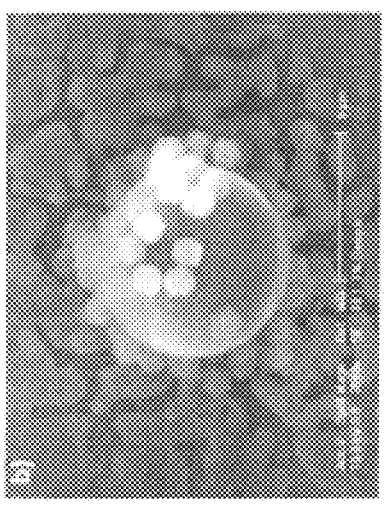
Figure 13A:
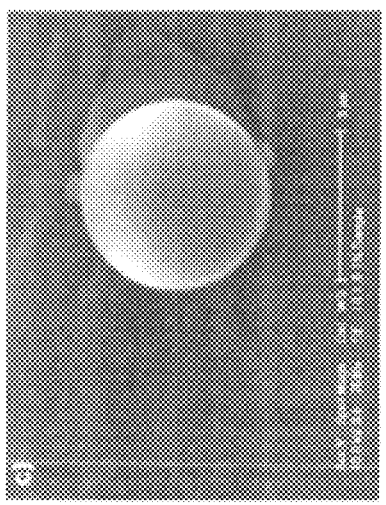

Scanning electron micrographs of the sandwich complexes are shown in FIGS. 13a-c. The three complexes shown were from samples with total biotin-coated particle concentrations of 2.88×10⁷, 2.88×10⁶, and 2.88×10⁵ particles/μL. FIG. 13a shows a reasonably dense coverage of the sphere by the superparamagnetic labelbeads, while FIG. 13b shows fewer beads, and FIG. 13c shows only two beads. This trend confirms that a greater number of superparamagnetic label beads are present with increasing amounts of biotin-coated particle.

Figure 14B:
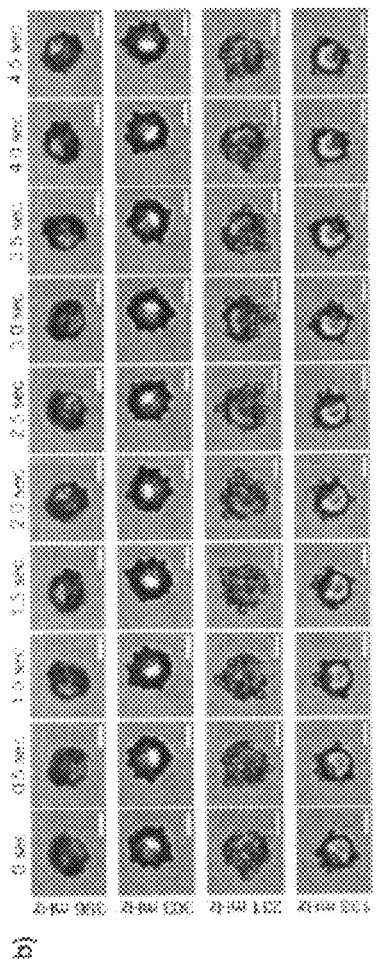
FIGS. 14a and 14b show an examination of the behavior of individual sandwich complexes under a constant rotating magnetic field. For example.
Figure 14A:
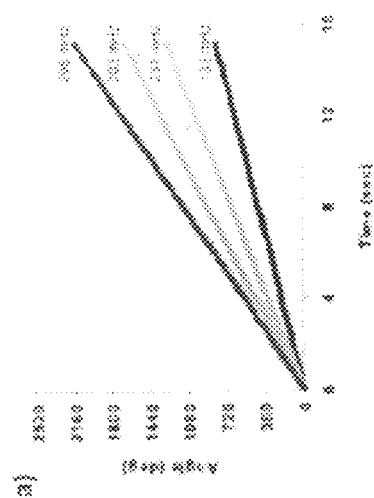

The frame-by-frame analysis of sandwich complexes, from four 15 s videos recorded at 20 frames per second, is shown in FIG. 14a. The angle of the sandwich complex in each frame is calculated against the first frame in the video, which is defined as the zero angle. One complete rotation is 360°. The sandwich complexes occasionally were out of focus, which caused the tracker to miss-track the complexes for those frames. These outlying points were removed from FIG. 14a, based on calculating the jackknife residuals for each point and discarding outliers, whose residuals exceeded the Bonferroni criteria. The four videos represent sandwich complexes with rotational frequencies of 133, 231, 303, and 396 MHz. The traces demonstrate the stability and consistency of the rotation of a sandwich complex during a 15 s observational period. Ten frames from each of the four videos, 0.5 s apart, are shown in FIG. 14b. These images show the sandwich complexes rotating clockwise.

Figures 15A, 15B:
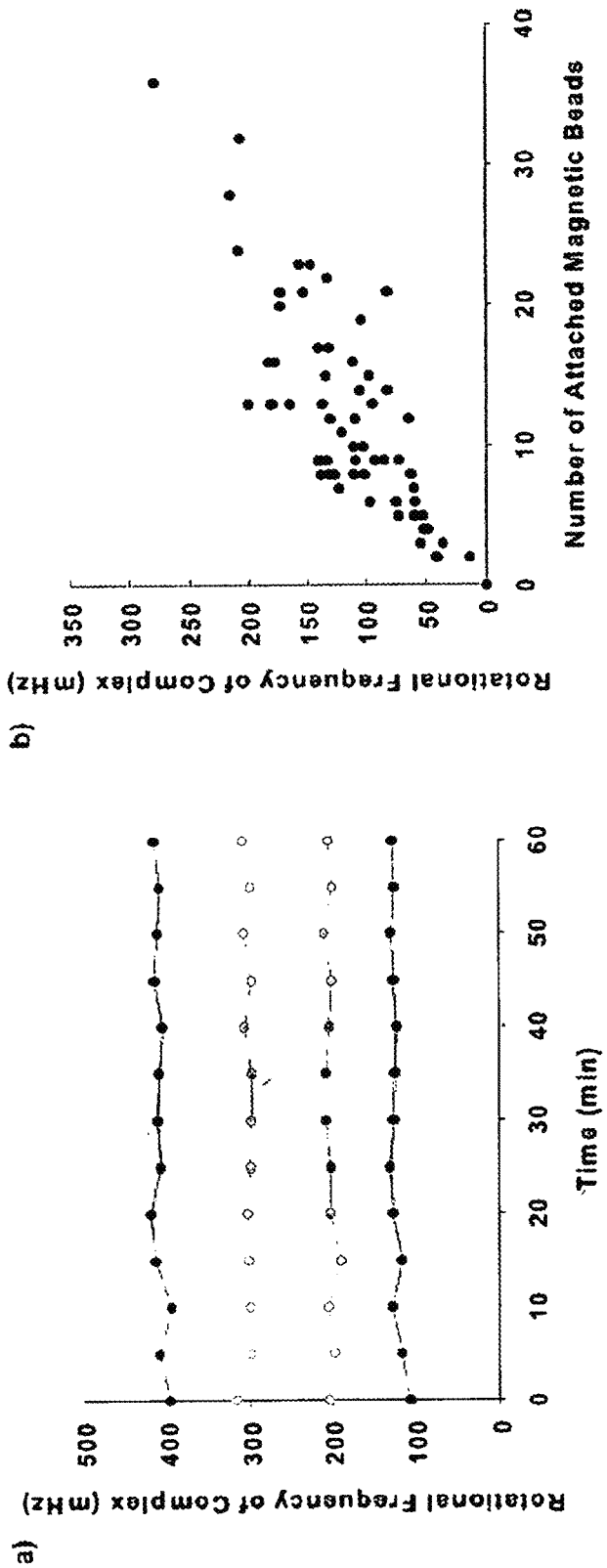
FIG. 15a illustrates the stability of the rotation of a sandwich complex over time. The rotational frequency of the complex was obtained every 5 min over a 60 min observational period. The mean±standard deviation of the rotational frequency for the four complexes over the observational period is 124.1±6.2, 203.3±5.1, 302.1±4.2, and 410.8±6.3 mHz.
FIG. 15b shows the relationship between the rotational frequency of the sandwich complex and the number of attached superparamagnetic beads. A linear trendline fits the data ($r^2=0.649$). Note that a sandwich complex will rotate with as little as two attached beads.

The stability of the rotational frequency of sandwich complexes was also measured. Sandwich complexes were observed for 60 min, with 15 s videos of the rotating complex captured every 5 min. Eight sandwich complexes were observed in total; four adhered to the coverslip before the end of the 60 min, and were excluded from the analysis. The use of PBS-TB decreased nonspecific adherence to the coverslips, but did not completely prevent it. The average (±SD) rotational frequencies of the four complexes determined from the videos over the observational period are: 124.1±6.2, 203.3±5.1, 302.1±4.2, and 410.8±6.3 MHz. The rotational frequencies of the four sandwich complexes are shown in FIG. 15a, and demonstrate that the rotational frequency of a rotating complex is stable over at least 60 min.

The behavior of individual sandwich complexes was found to determine the relationship between the rotational frequency and the number of attached superparamagnetic label beads. The number of superparamagnetic label beads attached to the complex was determined by visual inspection. The rotating magnetic field was then turned on, and the rotational frequency of each complex was measured. These results are shown in FIG. 15b. During observations, it was difficult to distinguish individual beads when more than 40 were on a solid phase sphere, so complexes with more than 40 attached beads were excluded from this analysis. It should also be noted that a complex will rotate with as little as two attached superparamagnetic label beads, which suggests that the theoretical lower detection limit of the system could be on the order of a few analyte molecules bound to the surface, for this solid phase sphere and magnetic label bead combination.

Figure 16:
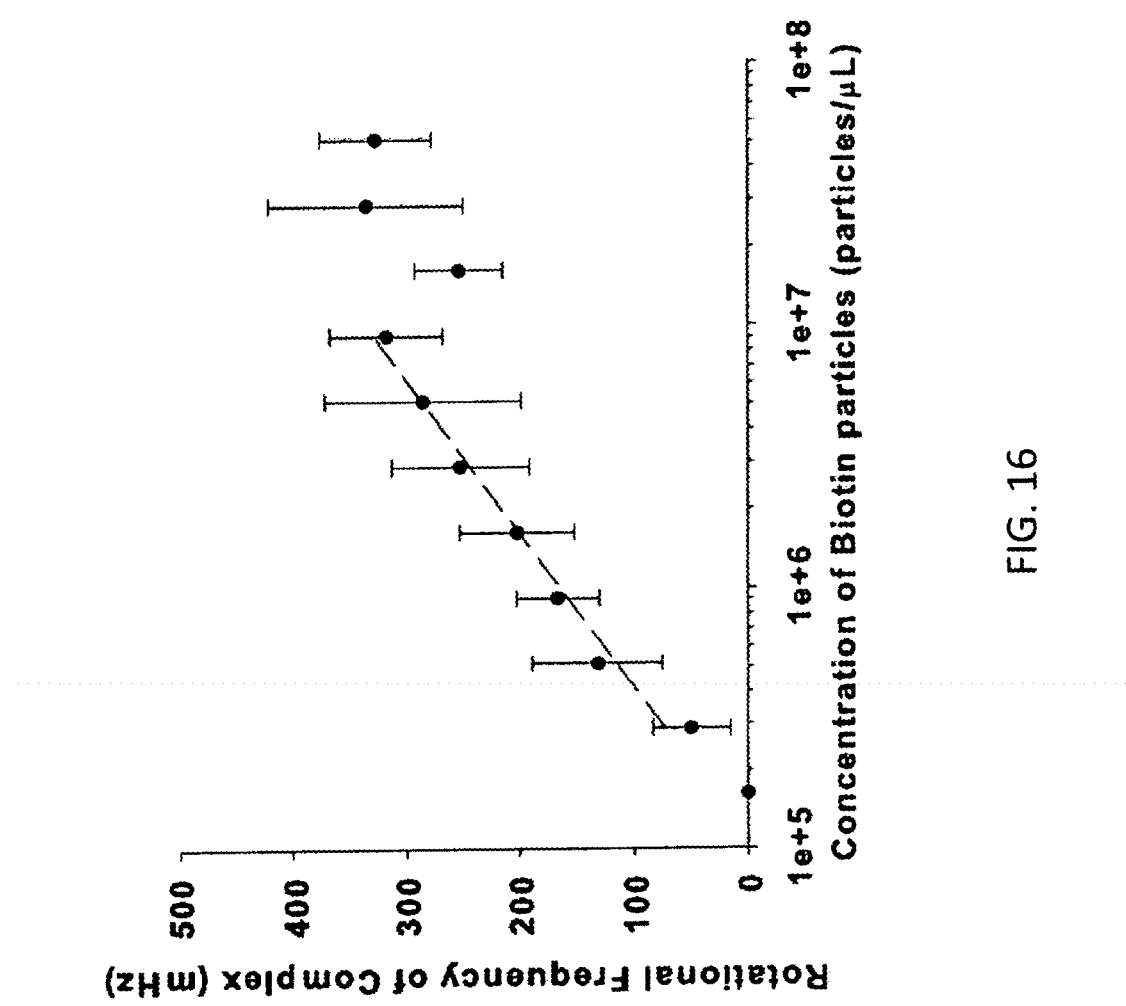
FIG. 16 shows a log-linear plot of the relationship between rotational frequency of the complex and concentration of an analyte incubated with the sphere. Each point represents an average of eight measurements (±SD). At high concentrations of biotin-coated particles, the sensor saturates and the rotational frequency plateaus. The sensor is linear over its dynamic range, indicated by the dashed line, $r^2=0.982$.

Having established the stability of the rotation of a sandwich complex, and the relationship between rotational frequency and the number of attached superparamagnetic label beads, Label-Acquired Magnetorotation (LAM) was shown to be capable of measuring the concentration of biotin-coated particles in solution. Sandwich complexes with a range of biotin-coated particle concentrations were prepared as described in the example above and transferred into a coverslip fluidic cell, and placed in a rotating magnetic field. Eight sandwich complexes from each concentration of biotin-coated particles were chosen at random and 15 s videos of each sandwich complex were recorded. Complexes that adhered to the surface of the coverslip were not considered for analysis (the number of attached magnetic labels did not appear to be a factor in determining sandwich complex-surface adhesion). The results are shown in FIG. 16. The rotational frequency of the sandwich complex increases with increasing biotin-coated particle concentration over the range $1.62 \times 10^5$-$9.70 \times 10^6$ biotin-coated particles/µL, and then plateaus at higher concentrations. This plateau is likely due to the saturation of the sphere by superparamagnetic beads labels. The lowest detected concentration of biotin-coated particles was $2.88 \times 10^5$ particles/µL. No formation of sandwich complexes, or rotation of the 6.7 µm spheres, was observed in control samples with no biotin-coated particles.

Thus, label-acquired magnetorotation can be used to detect the presence of biological targets. In some variations it may be desirable to control the size distribution of beads and spheres in particular the substrate spheres, which may reduce the variation (seen as the standard deviations in the data in FIGS. 15b and 16). This may allow improved comparison of one sandwich complex to another. For example, the 6.7 µm solid phase spheres in this example had a coefficient of variability in the diameter of 5.8% as determined by fluorescent activated cell sorting. Since the rotational frequency of the sphere depends on volume, this may result in up to a 17.4% variability in rotational frequency. Additionally, it may be desirable to normalize or regularize the magnetic moment of the label beads; in this example, the label particles (beads) are composed of magnetic nanoparticles embedded in a 1 µm non-magnetic bead, which exhibit bead-to-bead variability in magnetic content. Similarly, 2.8 µm superparamagnetic beads from the same manufacturer have been reported to have a variability in magnetic responsiveness (a combination of bead magnetic moment and shape factor) on the order of 30%. Observations suggest a similar variability for the 1 µm beads. These variabilities could be reflected in the scatter present in the data in FIG. 15. Averaging through multiple samples reduces this variability.

The potential sensitivity of this method was indicated by the rotation of a sandwich complex which was observed after the attachment of just two superparamagnetic label beads. The system described here presents a number of potential advantages for diagnostic applications. Label-acquired asynchronous magnetic bead rotation may be used in diagnostic devices, and may be applied to detect a wide range of targets, including biological targets such as proteins, viruses, bacteria, and cancer cells, or any other target associateable with an affinity molecule. For example, label-acquired magnetorotation may be used for the detection of antigens with antibodies, using a photodiode and a laser for monitoring rotation. Additionally, the system may be miniaturized, including operation with a microfluidic chip.

Thus, described herein is a new kind of biosensor, based on label-acquired asynchronous magnetic bead rotation. The sensor is based on a sandwich assay, with a nonmagnetic sphere as the solid phase and superparamagnetic beads as analyte labels and utilizes asynchronous magnetic bead rotation (AMBR). The rotational frequency of the sandwich complex in a rotating magnetic field depends on the concentration of the analyte present in the solution. This sensor demonstrates the potential for a simple and sensitive technique, with two orders of magnitude in dynamic range, which may improve with optimization of the parameters, including normalization of the sizes of the substrate particles and magnetic strengths of the magnetic label particles.

In some variations of the methods, devices and systems described herein, the sandwiches of substrate/analyte/magnetic label may be aggregated, clustered, or grouped. For example, multiple sandwiches may be joined by sharing one or more analytes between substrates. Clustering in this manner may be particularly helpful in detecting small quantities of material, where clustering of the substrate may have an amplification effect, making detection of rotation of the substrate easier. Alternatively, in some variations clustering is discouraged or reduced, which may be useful for concentration dependence of the assay.

Example—Protein Thrombin

The present techniques include a new signal transduction method, using a Label-Acquired Magnetorotation (LAM) as described herein, for the measurement of proteins in solution. The LAM technique has been used to detect the protein thrombin using aptamers, with an LOD (limit of detection) of 300 pM. The LAM technique was modeled after a sandwich assay, with a 10 µm nonmagnetic "mother" sphere as the capture component, and with 1 µm magnetic "daughter" beads as the labels. The protein-mediated attachment of daughter beads to the mother sphere forms a rotating sandwich complex. In a rotating magnetic field, the rotational frequency of a sandwich complex scales with the number of attached magnetic beads, which scales with the concentration of the protein present in solution. The result is the first instance of the detection of a protein using LAM.

The most common set-up for measuring the concentration of a protein in solution is the sandwich assay, where the target is first captured by an affinity molecule bound to a surface, and is then sandwiched by a signal transducer attached to another affinity molecule. Optical methods include sandwich-based ELISA, fluorescence signaling or quantum dots, and the non-sandwich based surface plasmon resonance methods. The electrochemical methods include sandwich-based amperometric enzymatic methods and non-sandwich-based impedimetric sensing.

Magnetic beads are advantageous for use as signal transducers because they are biologically inert, are physically stable under most biological environments, and biological materials have no native magnetism that could interfere with a signal from the beads. Due to these advantages, magnetic beads have been used as signal transducers in a variety of applications, including giant magnetoresistance (GMR), Hall probes, and magnetic relaxation. Additionally, magnetic beads have been used as carriers for magnetophoresis and to facilitate detection by other signal transduction methods. In contrast, the method described here uses optical detection of the magnetic behavior.

The beads used in this study are 1 μm commercial beads that exhibit superparamagnetic behavior (DynaBeads®). These beads are composed of maghemite (γ-Fe2O3) nanoparticles, with a mean diameter of 8 nm dispersed within a polymer bead. The beads are 25.5% Fe by mass. In the absence of a magnetic field, these beads have no net magnetization, but within a magnetic field, the magnetic moments of the beads align with the field and they become strongly magnetic.

The work presented here uses these beads in a rotating magnetic field. Previous studies have examined and characterized the behavior of these beads in alternating magnetic fields. It was first shown that in a one-dimensional alternating magnetic field, the dominant relaxation mechanism of such superparamagnetic beads is the Neel relaxation of the nanoparticles embedded within the bead. It was later shown that in a two-dimensional rotating magnetic field, at high driving frequencies, the dominant mechanism driving the rotation of these same beads is also related to Neel relaxation. Brownian rotational effects are not significant for these beads because the time constant for the Brownian relaxation of a sphere with diameter on the order of a micron is on the order of seconds, while the time constant for the Neel relaxation of the inner magnetic nanoparticles is on the order of nanoseconds.

In a two-dimensional rotating magnetic field, at low driving frequencies, magnetic beads are able to rotate synchronously with the field. At higher driving frequencies (above the critical frequency) these beads are not able to stay in phase with the field, and rotate asynchronously. In the asynchronous regime, the rotational frequency of the bead depends on a number of factors, including the magnetic moment of the bead, the amplitude and frequency of the driving field, the hydrodynamic volume of the bead, and the viscosity of the solution. This asynchronous rotation has already been demonstrated to be a useful tool for making biological measurements, specifically for monitoring the growth and antibiotic susceptibility of bacteria.36-39

Thrombin is a coagulation factor that is the first step in the coagulation cascade that leads to the formation of a blood clot, so as to stem blood loss. Aptamers are single- or double-stranded nucleic acid sequences that bind to proteins through favorable electrostatic interactions, with an affinity similar to that of an antibody. One of the earliest aptamers to be identified binds to the fibrin exosite on thrombin, and has the following 15-base pair sequence: 5'-GGTTGGT-GTGGTTGG-3' (SEQ ID NO: 1). Later, a second, 29-base pair sequence against thrombin was identified, which binds to the heparin exosite: 5'-GTCCGTGGTAGGGCAGGT-TGGGGTGAC-3' (SEQ ID NO: 2). Since these aptamers bind to opposite sides of the thrombin molecule, they represent an ideal system for the development of an aptamer-based sandwich assay, and have been used in the development of many such assays.

Figure 17:
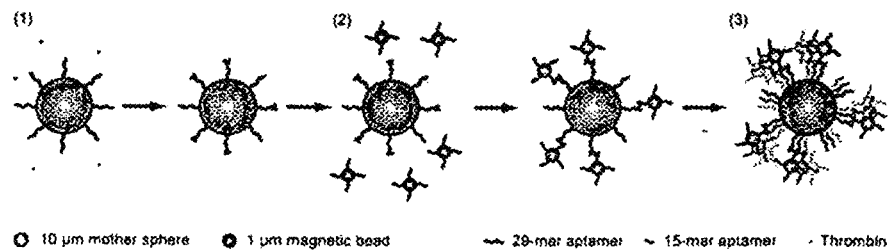
FIG. 17 illustrates a schematic of LAM with thrombin as the analyte. (1) 10 μm nonmagnetic mother spheres coated with the 29-mer anti-thrombin aptamer are mixed with thrombin, which binds to the mother spheres. (2) 1 μm magnetic beads coated with the 15-mer anti-thrombin aptamer are mixed with the thrombin-coated mother spheres. The magnetic beads bind to the thrombin attached to the mother sphere, forming a sandwich complex. (3) The sandwich complex is transferred to a rotating magnetic field, where the rotational frequency of the sandwich complex depends on the number of attached magnetic beads.

A schematic of LAM is shown in FIG. 17. The mother spheres used were 10 μm nonmagnetic streptavidin-coated ProActive microspheres (Bangs Labs, Fishers, Ind.). The daughter beads used were Dynal MyOne 1 μm streptavidin-coated DynaBeads that exhibit superparamagnetic behavior (Invitrogen, Carlsbad, Calif.). Human α-thrombin was purchased from Haematologic Technologies (Essex Junction, Vt.). Biotinylated aptamers (with a 5' polyT$_{20}$ tail for improved binding) were purchased from Integrated DNA Technologies (Coralville, Iowa). Salts (NaCl, KCl, MgCl$_2$, EDTA and Tris-HCl) and Tween-20 were purchased from Sigma Aldrich (St. Louis, Mo.). Bovine serum albumin (BSA) Blocker solution was purchased from Thermo Scientific (Waltham, Mass.). Zero-thickness glass coverslips were obtained from Electron Microscopy Sciences (Hatfield, Pa.). OPI Top Coat clear nail protector was purchased from OPI Products Inc. (North Hollywood, Calif.). Formulations for wash buffer, aptamer binding buffer, and thrombin binding buffer (containing 0.1% BSA, and with the addition of 10 mM KCl) were based on previously published work.

An aliquot of 50 μL of the magnetic beads was washed three times by magnetic separation in 200 μL of wash buffer, then resuspended in 500 μL of aptamer binding buffer, at a concentration of 1 mg/mL beads in a microcentrifuge tube. An aliquot of 50 μL of the mother spheres was washed three times by centrifugation in 200 μL of wash buffer, then resuspended in 1 mL of aptamer binding buffer, at a concentration of 0.5 mg/mL spheres. A 10 μL aliquot of biotinylated-15-mer thrombin binding aptamer was added to the superparamagnetic beads, and a 10 μL aliquot of biotinylated-29-mer thrombin binding aptamer was added to the mother spheres. The two solutions were briefly vortexed then incubated on an end-over-end rotator for 1 hour. They were then washed (by magnetic separation and centrifugation, respectively) three times and resuspended in thrombin binding buffer. An aliquot of human α-thrombin was serially diluted over a concentration range of 50 nM to 100 pM in thrombin binding buffer. In a separate tube, 100 μL of thrombin solution were mixed with 40 μL of mother sphere solution, and then incubated on an end-over-end rotator for 90 minutes. Finally, 10 μL of magnetic bead solution were added to the mother spheres and thrombin and incubated on an end-over-end rotator for 90 minutes.

Microfluidic flow cells were prepared from two zero-thickness glass coverslips (the bottom coverslip was coated with a thin layer of clear nail protector, to reduce particle sticking) separated by a single piece of double-sided Scotch tape (3M, St. Paul, Minn.). The solution containing the mother spheres and the magnetic beads was diluted with 140 μL of 0.2% Tween-20, and 20 μL of this solution were pipetted into the coverslip flow cell. The coverslip flow cell was then placed in a rotating magnetic field (amplitude 1.25 mT, frequency 200 Hz) built from two pairs of orthogonally-oriented Helmholtz coils driven by a pair of sinusoidal waves 90 degrees out of phase with each other. The magnetic field was located on top of an IX71 inverted microscope (Olympus, Melville, N.Y.). The rotation of the sandwich complexes was observed through a 100× oil-immersion objective, imaged through a Basler piA640-210 gm camera (Basler, Highland, Ill.) and recorded by an in-house program written in LabVIEW (National Instruments, Austin, Tex.). Videos were analyzed using the St. Andrews particle tracker and an in-house program written in MATLAB.

The theory governing the behavior of superparamagnetic particles and beads in rotating magnetic fields has been discussed in detail elsewhere. Briefly, starting from the equation for the magnetic torque, τ=m×B, where m is the magnetic moment of the bead and B is the external magnetic field, assuming steady-state rotation (allowing for the equating of rotational driving forces with drag forces, $$\tau = \kappa \eta V_H \frac{d\theta}{dt},$$

where κ is the shape factor (equal to 6 for a sphere), η is the viscosity of the surrounding fluid, and $V_H$ is the hydrodynamic volume), and making some simple substitutions, $B=\mu_0 H$, $m=MV_m$, $M=\chi H$ and $\chi=\chi'-i\chi''$, (where H is the magnetizing field, $\mu_0$ is the permeability of free space, M is the volume magnetization, $V_m$ is the volume of the bead's magnetic material, χ is the bead susceptibility, χ' is the real component of the bead susceptibility and χ'' is the imaginary component of the bead susceptibility) we can get an expression for the rotational frequency dθ/dt:

$$\frac{d\theta}{dt} = \frac{1}{\kappa \eta V_H} \mu_0 V_m \chi'' H^2 \quad (1)$$

The definition of imaginary susceptibility, χ'', is $$\chi'' = \chi_0 \frac{\Omega \tau_N}{1 + \Omega^2 \tau_N^2},$$

where $\chi_0$ is the DC susceptibility, Ω is the frequency of the driving field. The definition of Neel relaxation time, $\tau_N$, is $$\tau_N = \tau_0 \exp\left(\frac{KV_p}{k_B T}\right),$$

where $\tau_0$ is the attempt frequency, K is the anisotropy constant (equal to $5\times 10^4$ J/m$^3$ for maghemite nanoparticles), $V_p$ is the volume of the maghemite nanoparticles, $k_B$ is Boltzmann's constant, and T is the ambient temperature. The magnetic nanoparticles are not perfectly uniform; for a size distribution with n intervals, with average nanoparticle volume $V_p$, the total volume of nanoparticles in the distribution is $V_n$. The expression for Neel relaxation time, $\tau_N$, can be substituted into the expression for imaginary susceptibility, χ'', which, along with considering the effects of the nanoparticle size distribution, can then be substituted into equation (1) to create a single expression describing the rotation of a superparamagnetic object in a magnetic field:

$$\frac{d\theta}{dt} = \frac{1}{\kappa \eta V_H} \mu_0 V_m H^2 \chi_0 \frac{1}{\sum_n V_n^2} \sum_n \frac{\Omega \tau_0 \exp\left(\frac{KV_p}{k_B T}\right)}{1 + \Omega^2 \exp\left(\frac{2KV_p}{k_B T}\right)} V_n^2 \quad (2)$$

In the low driving frequency (Ω<<1 kHz) regime used in this paper, $\Omega^2$ exp $$\left(\frac{2KV_p}{k_B T}\right) << 1,$$

so equation (2) can be simplified:

$$\frac{d\theta}{dt} = \frac{1}{\kappa \eta V_H} \mu_0 V_m H^2 \chi_0 \frac{1}{\sum_n V_n^2} \sum_n \Omega \tau_0 \exp\left(\frac{KV_p}{k_B T}\right) V_n^2 \quad (3)$$

To test whether the sandwich complexes follow the model of equation (3), we observed the response of the sandwich complexes to changes in amplitude and frequency. Holding all variables except for field amplitude constant, equation (3) reduces to $$\frac{d\theta}{dt} \propto H^2.$$

Figures 18A, 18B:
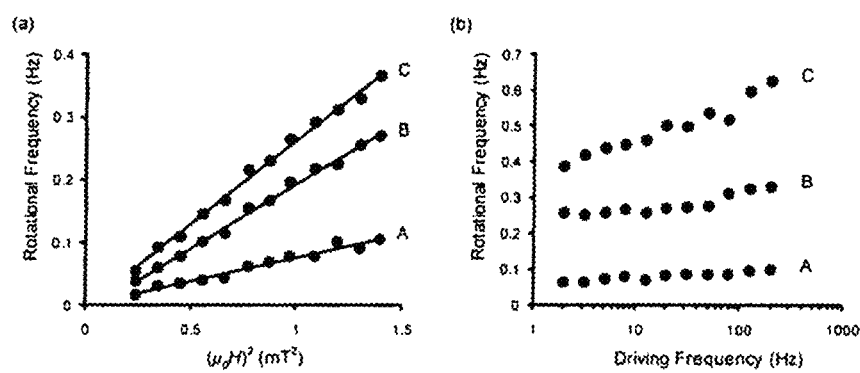
FIG. 18a illustrates an amplitude response curves showing that the rotational frequency of a sandwich complex is proportional to the square of the amplitude of the driving field (with B=μ0H). The data are fit with a linear trendline with r2 values of (A) 0.968, (B) 0.995, and (C) 0.994.
FIG. 18b illustrates a frequency response curves showing that the rotational frequency of a sandwich complex increases with an increase in the frequency of the driving field.

FIG. 18a shows indeed that the rotational frequency of a sandwich complex is directly proportional to the square of the amplitude of the driving field. Holding all variables constant except for field driving frequency, equation (3) reduces to $$\frac{d\theta}{dt} \propto \Omega.$$

FIG. 18b shows that the rotational frequency of a sandwich complex does increase with the frequency of the driving field, but it does not exactly demonstrate the linear relationship that equation (3) suggests.

We examined the stability of the rotation of sandwich complexes over 60 minutes of observation. The rotational frequency of four sandwich complexes was measured every 5 minutes for 60 minutes, as shown in FIG. 19a. The coefficient of variation (standard deviation divided by the mean, times 100%) of the complexes (A-D) was 3.3%, 2.5%, 1.5% and 1.6%, respectively, demonstrating that the rotation of a sandwich complex is fairly stable over a 60 minute observation period. All other measurements reported here were made within an hour of the sandwich complexes being injected into the coverslip fluidic cell.

A dose-response curve of LAM used for measuring the concentration of thrombin in solution is shown in FIG. 19b. At each thrombin concentration, the rotation of 15 sandwich complexes was measured, and each point in the figure represents the average of those 15 measurements (±standard deviation). The data was fit using the four-parameter logistic Hill equation. The dynamic range of the curve extends from about 1 nM to about 20 nM. Above 20 nM, the curve plateaus. Below 1 nM, there is still a detectable signal down to 300 pM. In the 300 pM to 1 nM range, there was still binding of beads to the mother sphere, but there was no significant difference between the different concentrations. Below 300 pM, no binding of beads to the mother sphere was observed. Similarly, in a control sample (no thrombin), there was also no binding detected. In the absence of the aptamers thrombin does not bind to the spheres and beads. FIG. 19b demonstrates the viability of LAM as a tool for measuring the concentration of a protein in solution, with an LOD (limit of detection) of 300 pM.

Screenshots of the rotation of five of the sandwich complexes from FIG. 19b are shown in FIG. 20. These images show that the number of beads attached to each complex increases with the concentration of thrombin, and that the rotational frequency of the complexes increases with the number of attached beads. These images also show that a qualitative estimate of the protein concentration can be made merely by looking at the complexes under a microscope, without using rotation.

One of the advantages of using the thrombin aptamers are their popularity; many groups have used these aptamers for demonstration of signal transduction techniques. When examining other methods that are sandwich-based and use single-step (non-amplified) methods, reported LODs typically are in the 0.1-1 nM range, including electrochemical detection, quantum dots, Si-nanowire FETs, and fluorescent molecular beacons. There are many clinically relevant biomarkers found in plasma at concentrations around 1 nM. Within this context, we believe that LAM is certainly competitive with other detection technologies. Moreover, LAM has the advantage of simplicity, robustness and low cost, without requiring sensitive optical readers or other expensive and stationary sensing equipment.

We generated a model in MATLAB to simulate the optimal performance of LAM, assuming perfect mixing and no nonspecific interactions, based on a previously reported two-site immunoassay model. Considering only specific interactions, there are two primary reactions that take place in our system:

(4)

(5)

where P is the protein of interest, $Q_1$ is the capture aptamer, and $Q_2$ is the detection aptamer. Also, there are two possible side reactions:

(6)

(7)

The model is carried out in two parts, capture and detection. In the capture phase, only equation (5) is considered. After the capture reaction has reached equilibrium, the detection phase commences, in which equations (5)-(8) are all considered. The rate constants for the thrombin aptamers were obtained from previously published work. The model is generated by simultaneously solving the six differential equations below:

$$\frac{d[Q_1]}{dt} = -k_1[Q_1][P] + k_{-1}[Q_1P] - k_4[Q_1][Q_2P] + k_{-4}[Q_1PQ_2] \quad (9)$$

$$\frac{d[Q_2]}{dt} = -k_3[Q_2][P] + k_{-3}[Q_2P] - k_2[Q_1P][Q_2] + k_{-2}[Q_1PQ_2] \quad (10)$$

$$\frac{d[P]}{dt} = -k_1[Q_1][P] + k_{-1}[Q_1P] - k_3[Q_2][P] + k_{-3}[Q_2P] \quad (11)$$

$$\frac{d[Q_1P]}{dt} = k_1[Q_1][P] - k_{-1}[Q_1P] - k_2[Q_1P][Q_2] + k_{-2}[Q_1PQ_2] \quad (12)$$

$$\frac{d[Q_2P]}{dt} = k_3[Q_2][P] - k_{-3}[Q_2P] - k_4[Q_1][Q_2P] + k_{-4}[Q_1PQ_2] \quad (13)$$

$$\frac{d[Q_1PQ_2]}{dt} = k_2[Q_1P][Q_2] + k_4[Q_1][Q_2P] - (k_{-2} + k_{-4})[Q_1PQ_2] \quad (14)$$

Figure 21:
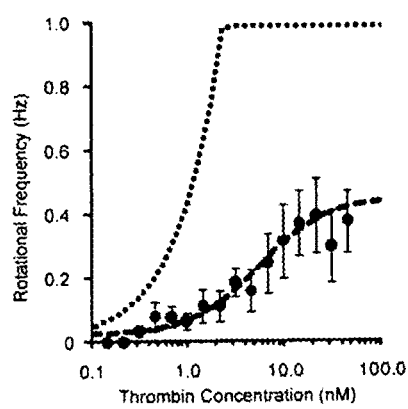
FIG. 21 is a plot of the simulated dose-response curve (dotted line) for LAM from a model based on the binding kinetics of the aptamers with thrombin. Also included in the plot are experimental data (dots), from FIG. 19b, and a logistic curve fit (dashed line). The abrupt plateau at the top of the predicted dose-response curve represents the saturation of the sensor.

The simulated dose-response curve based on this model is shown in FIG. 21. Deviations of the experimental data from this simulated dose-response curve could be due to nonspecific interactions between the aptamers and other proteins in solution, imperfect mixing, suboptimal aptamer-bead attachment, or experimental error. The rather abrupt plateau at the top of the dose-response curve is due to the saturation of the mother spheres with magnetic beads before saturation with thrombin; only a few hundred beads can bind to the mother sphere, but over a million thrombin molecules could bind to the mother sphere.

It is our long term goal to develop LAM into a signal transduction method that is suitable for use in a point-of-care clinical setting. In order to achieve this goal, several additional steps must be taken. We plan to translate LAM off the microscope and measure the rotation of the sandwich complex using a simple, compact-disc-like, laser-and-photodiode setup, together with automated and self-contained mixing, in a microfluidic chip. We also plan to reproduce these results in a biological fluid medium, such as serum. We believe that, after additional development, LAM will be an attractive tool for use, because it will not require fluorescence readers or a microscope, and the actual detector (the laser and photodiode) would be low-cost. We recognize that these goals will require additional work. The goal of this paper is to demonstrate the feasibility of LAM as a signal transduction method for measuring the concentration of a protein in solution, for possible future applications as a point-of-care signal transduction method.

Thus, as described label-acquired magnetorotation is a viable signal transduction method for measuring the concentration of a protein in solution. We have shown that the amplitude and frequency response of a sandwich complex generally follow the behavior predicted by the equations that describe superparamagnetic bead behavior.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed is:

1. A method of detecting a target, the method comprising:
 (a) contacting the target which is immobilized on a non-magnetic substrate particle with a plurality of magnetic particles under conditions in which the magnetic particles are capable of associating or complexing with the target, wherein the diameter of the one or more magnetic particles is smaller relative to the diameter of the non-magnetic substrate particle;
 (b) applying a rotating magnetic field to the immobilized target which is associated or complexed with the magnetic particles; and
 (c) detecting rotation in the magnetic field arising from association or complex formation of one or more of the magnetic particles associated or complexed with the immobilized target, wherein detection of rotation and/or rate of rotation of the target indicates presence of the target.

2. The method of claim 1 wherein the target is a target cell.

3. The method of claim 2 wherein a change in the rotation of the target cell over time indicates growth of the target cell.

4. The method of claim 2 wherein the target cell is in a population of target cells.

5. The method of claim 4 wherein the population is an aggregate of cells.

6. The method of claim 4 wherein the population of target cells contain target cells of different morphology.

7. The method of claim 6 wherein the population of target cells rotate at different rotation rates based on the different morphologies.

8. The method of claim 6 wherein the different morphology is a cellular deformation.

9. The method of claim 8 wherein the cellular deformation is a cell surface protrusion and/or is due to a genetic or biochemical change within one or more cells of the population.

10. The method of claim 2 wherein the target cell is a cancer cell.

11. The method of claim 2 wherein association is effected by one or more of the magnetic particles being internalized by the cell.

12. The method of claim 11 wherein the magnetic particles are internalized in a non-specific manner.

13. The method of claim 2 wherein magnetic particles associated with the cell induce rotation of the cell.

14. The method of claim 1 wherein one or more of the magnetic particles comprises a targeting moiety and association is effected by binding of the targeting moiety to the target.

15. The method of claim 14 wherein the targeting moiety is a peptide, an antibody, a nucleic acid, an aptamer or a combination thereof.

16. The method of claim 1 wherein the target is an analyte.

17. The method of claim 16 wherein the analyte is a biological analyte.

18. The method of claim 17 wherein the biological analyte is a protein or a nucleic acid.

19. The method of claim 18 wherein the analyte is thrombin.

20. The method of claim 16 wherein the analyte is non-biological.

21. The method of claim 20 wherein the non-biological analyte is a metal.

22. The method of claim 16 wherein the magnetic particles and the substrate particle bind the target to form the complex between the magnetic particle, the target and the substrate particle.

23. The method of claim 22, further comprising determining a rate of rotation of the complex to determine concentration of the analyte.

24. The method of claim 23 wherein a higher concentration of analyte in the sample produces a faster rotation of the complex relative to a lower concentration of analyte in a control sample.

25. The method of claim 1 wherein the diameter of the one or more magnetic particles is from about 0.01 micrometers (μm) to about 5 μm in diameter, and the diameter of the non-magnetic substrate particle is from about 5 μm to about 100 μm in diameter.

* * * * *